United States Patent
Patel et al.

(10) Patent No.: US 11,513,111 B2
(45) Date of Patent: Nov. 29, 2022

(54) WAX RISK ASSESSMENT AND MITIGATION USING ADVANCED DATA ANALYTICS AND PIPE FLOW MODELING

(71) Applicant: BL Technologies, Inc., Minnetonka, MN (US)

(72) Inventors: Nimeshkumar Kantilal Patel, The Woodlands, TX (US); Hitesh Ghanshyam Bagaria, Tomball, TX (US); Guoliang Wang, Shanghai (CN); Xiaoan Xie, Shanghai (CN); Xiao Zhang, Shanghai (CN); Yun Peng, Shanghai (CN); Wenqing Peng, Shanghai (CN); Sheng Zheng, The Woodlands, TX (US); John Brian McDermott, Niskayuna, NY (US); Peter Larry Perez Diaz, Tomball, TX (US)

(73) Assignee: BL Technologies, Inc., Minnetonka, MN (US)

( * ) Notice: Subject to any disclaimer, the term of this patent is extended or adjusted under 35 U.S.C. 154(b) by 438 days.

(21) Appl. No.: 16/604,199

(22) PCT Filed: Apr. 10, 2017

(86) PCT No.: PCT/CN2017/079875
§ 371 (c)(1),
(2) Date: Oct. 10, 2019

(87) PCT Pub. No.: WO2018/187898
PCT Pub. Date: Oct. 18, 2018

(65) Prior Publication Data
US 2020/0033317 A1 Jan. 30, 2020

(51) Int. Cl.
*G01N 33/28* (2006.01)
*C10G 75/02* (2006.01)
(Continued)

(52) U.S. Cl.
CPC ......... *G01N 33/2835* (2013.01); *C10G 31/00* (2013.01); *C10G 75/02* (2013.01); *C10G 75/04* (2013.01); *G01N 33/2876* (2013.01)

(58) Field of Classification Search
CPC .. C10G 29/00; C10G 31/00; C10G 75/00–04; G01N 33/2835; G01N 33/2876; G01N 33/2882
See application file for complete search history.

(56) References Cited

U.S. PATENT DOCUMENTS

| | | | |
|---|---|---|---|
| 6,087,662 A | 7/2000 | Wilt et al. | |
| 7,813,894 B2 * | 10/2010 | Prasad | G06Q 10/04 702/182 |

(Continued)

FOREIGN PATENT DOCUMENTS

| | | |
|---|---|---|
| CN | 101558364 | 10/2009 |
| WO | 2017/023795 | 2/2017 |
| WO | 2017/100224 | 6/2017 |

OTHER PUBLICATIONS

First Office Action issued in related Chinese Application No. 201780089491.3, 35 pages.
(Continued)

*Primary Examiner* — Renee Robinson
(74) *Attorney, Agent, or Firm* — Meunier Carlin & Curfman LLC

(57) ABSTRACT

Described herein are systems and methods for evaluating and mitigating the wax risks of a given hydrocarbon composition such as crude oil. The disclosed systems and methods enable rapid and ready prediction of wax risks using algorithms based on a small sample of the hydrocarbon composition. The wax risks are predicted using predictive models developed from machine learning. The disclosed systems and methods include mitigation strategies for
(Continued)

wax risks that can include chemical additives, operation changes, and/or hydrocarbon blend.

21 Claims, 14 Drawing Sheets

(51) Int. Cl.
    *C10G 75/04*     (2006.01)
    *C10G 31/00*     (2006.01)

(56) References Cited

U.S. PATENT DOCUMENTS

| | | |
|---|---|---|
| 2002/0050355 A1 | 5/2002 | Kowalewski et al. |
| 2009/0192768 A1 | 7/2009 | Zuo et al. |
| 2018/0079977 A1* | 3/2018 | Solomon .................. F17D 1/17 |

OTHER PUBLICATIONS

International Search Report and Written Opinion dated Jan. 16, 2018, from International Application No. PCT/CN2017/079875, 12 pages.

Jin, W. "Study on the Wax Deposition and Prediction Method of Waxy Crude Oil", Chinese Doctoral Dissertations Full-text Database Engineering Science and Technology I, Mar. 15, 2017, No. 3, English Abstract.

Sai, Y. "Study on Wax Depostion Model of Waxy Crude Pipelines", Chinese Master's Theses Full-text Database Engineering Science and Technology I, Feb. 15, 2015, No. 2.

Obanijesu, E. O. et al. "Artificial Neural Network's Prediction of Wax Deposition Potential of Nigerian Crude Oil for Pipeline Safety", Petroleum Science and Technology, Oct. 31, 2008, vol. 26.

Li, S. et al. "Review of Measurement Techniques for Wax Precipitation Characteristics of Petroleum Fluids", ACTA Petrolei Sinica (Petroleum Processing Section), Dec. 31, 2016, No. 6, vol. 32, English Abstract.

Wenbo, et al. "Study of the Wax Deposition and Prediction Method of Waxy Crude Oil", Southwest Petroleum University, Mar. 15, 2017, pp. 1-125.

Xie, Y. et al. "A prediction method for the wax deposition rate based on a radial basis function neural network", Petroleum 3 (2017) 237-241.

Zheng, S. et al. "Wax Deposition Modeling with Considerations of Non-Newtonian Characteristics: Application on Field-Scale Pipeline", Energy Fuels 2017, 31, 5011-5023.

Perez, P.L. et al. "Mitigating Wax Deposition From Crude Oils: Correlations Between Physical-Chemical Properties of Crude Oils and the Performance of Wax Inhibitors", OTC-27255-MS.

First Examination Report dated Feb. 2, 2022, from Indian Application No. 2019470425895, 6 pages.

Office Action, dated Jul. 25, 2022, received in connection with corresponding CN Patent Application No. 201780089491.3 (English translation).

Office Action, dated Jul. 22, 2022, received in connection with corresponding MY Patent Application No. PI2019004714.

\* cited by examiner

WAX RISK ASSESSMENT AND MITIGATION USING ADVANCED DATA ANALYTICS AND PIPE FLOW MODELING

FIELD OF THE INVENTION

Disclosed herein are methods of analyzing hydrocarbon samples, including methods of analyzing hydrocarbon samples to predict wax risks. More specifically, methods and systems disclosed herein provide for rapidly and easily determining wax risks of a hydrocarbon composition as well as determining the optimal wax inhibitors/dispersants/dissolvers, and thereby improving the mitigation of wax risks in hydrocarbon production, transportation, refining, and refined hydrocarbon processing and use by identifying the hydrocarbon streams presenting the risk of wax formation and/or chemical treatments for the hydrocarbon stream of interest.

BACKGROUND

The majority of hydrocarbons found on earth naturally occur in crude oil, where decomposed organic matter provides an abundance of carbon and hydrogen which, when bonded, can catenate to form paraffin molecules with chain length as long as 100 carbons. Paraffin molecules precipitate and form solids as temperature decreases. Precipitation of paraffin wax can lead to deposition of wax on well-bore tubing, oil transportation pipelines as well as during refinery processing and refined hydrocarbon production, processing, handling, storage, and use, including a tank-farm, a cold preheat train, a desalter, a hot preheat train, a crude heater/furnace, a crude distillation unit, a vacuum unit furnace, a vacuum distillation unit, and downstream processing units such a hydrotreater, a hydrocracker, fluid catalytic cracking (FCC), a visbreaker, a coker, etc. Deposition and accumulation of a phase separated from the mobile phase in a refining operation is also known as fouling. Unwanted materials such as scale, algae, suspended solids, and insoluble salts can deposit on the surfaces of processing equipment such as boilers and heat exchangers. Paraffin deposition is a severe challenge and has significant impacts on the efficiency, safety and economics of hydrocarbon production, transportation, refining and refined hydrocarbon production, processing, handling, storage, and use.

The wax deposit attached to the inner walls of oil transportation pipelines require regular remediation, e.g., mechanical removal, also known as "pigging". A weekly pigging operation generates a typical yearly operational cost of over $30 million USD. Severe and reoccurring wax deposition can even lead to abandonment of the oil field at a cost of over $100 million USD.

Wax deposition can also be encountered in refinery equipment. For example, crude preheat train fouling due to wax deposition decreases refining efficiency, both by requiring additional energy inputs to overcome temperature reduction and interrupting normal refinery operation for cleaning and other maintenance.

Methods for evaluating the fouling potential of a hydrocarbon sample have been explored. Generally, these methods rely on analysis of the liquid hydrocarbon itself. However, these methods are typically time consuming.

Furthermore, mitigation of fouling and wax/parrafin deposition can be time-consuming and/or problematic. The selection of wax inhibitors for crude oils has traditionally been performed using a "trial-and-error" approach. The performance of a series of chemical additives is evaluated using bench-top tests, such as pour point, cold finger, and rheology, and the best chemistry/dosage recommendations are made. Since the actual crude oil might not be readily available, sometimes the comparative evaluations are performed using synthetic waxy fluids or, in the best case, using a battery of crude oils with physical and chemical properties resembling the crude oil that will be treated in the field. The tests are usually complemented with empirical or heuristical know-how about the influence of crude oil properties, field conditions, etc., on the expected field performance.

The problem with the trial-and-error approach to the selection of wax inhibitors and pour point depressants is associated to the risks of selecting the wrong chemical. It is not uncommon to find that wax inhibitors that show good performance with synthetic waxy fluids perform poorly or do not perform at all with real fluids. It is not uncommon either to observe that a wax inhibitor that was effective with a certain type of crude oil, is not as effective in another. Thus, it is generally accepted that the effectiveness of wax inhibitor is limited, and has to be evaluated on a case by case basis. This crude oil "specificity" of wax inhibitor has plagued the industry for a long time, and it has been the subject of several investigations. Further, the trial-and-error method can be time-consuming. For example, a traditional cold finger test requires hours for only a single data. Small sample volume needed for the one single test (several mL) is another advantage while traditional cold finger test requires 80-100 mL crude for a single data.

There remains a strong need for a method that enables refiners to reliably and rapidly predict potential fouling of a given hydrocarbon. There remains a need for robust method would allow oil producers/refiners to select a hydrocarbon with less fouling potential, as well as to treat a hydrocarbon with the appropriate chemical treatment to minimize fouling.

SUMMARY

Disclosed herein are systems and methods of rapidly and easily evaluating the wax risks of a given hydrocarbon composition.

Disclosed herein are embodiments of a method of determining and mitigating wax risk of a hydrocarbon composition. One aspect of the method comprises obtaining a sample of the hydrocarbon composition; analyzing the sample of the hydrocarbon composition to determine one or more attributes of the sample of the hydrocarbon composition; developing one or more predictive models of a hydrocarbon production, transportation, refining, refined hydrocarbon production, processing and use process for the hydrocarbon composition entering the hydrocarbon production, transportation, refining, refined hydrocarbon production, processing and use process based on the analysis of the sample of the hydrocarbon composition; determining wax risks based on the developed one or more predictive models; and mitigating one or more of the determined wax risks.

Alternatively or optionally, the method may comprise developing a pipe flow model for a pipeline and determining wax risks in the pipeline based on the pipe flow model and the determined wax risks. In one aspect, developing the pipe flow model for the pipeline comprises using parameters and operating conditions of the pipeline when developing the pipe flow model. The parameters and operating conditions of the pipeline comprise real-time parameters and operating conditions of the pipeline. Alternatively, the parameters and operating conditions of the pipeline comprise historical parameters and operating conditions of the pipeline.

Alternatively or optionally, mitigating one or more of the determined wax risks may comprise determining chemical additives to mitigate one or more of the determined wax risks. In some aspects, determining chemical additives to mitigate one or more of the determined wax risks may comprise selecting one or more chemical additives based on matching precipitation characteristics between the one or more chemical additives and wax in the hydrocarbon composition, and/or the attributes related to composition of the hydrocarbon. In some aspects, determining chemical additives to mitigate one or more of the determined wax risks may comprise determining a blend of chemical additives to mitigate one or more of the determined wax risks. In some aspects the blend of chemical additives is determined based on matching precipitation characteristics between the blend of chemical additives and wax in the hydrocarbon composition. The wax in the hydrocarbon composition may be determined based on the analysis of the sample of the hydrocarbon composition to determine the one or more attributes of the sample of the hydrocarbon composition.

Alternatively or optionally, determining chemical additives to mitigate one or more of the determined wax risks may comprise developing qualitative chemical additive predictive models for selecting one or more chemical additives based on the analysis of the sample of the hydrocarbon composition to determine the one or more attributes of the sample of the hydrocarbon composition. In some aspects, the qualitative chemical additive predictive models are developed using a chemical additive machine learning algorithm. The chemical additive machine learning algorithm may include one or more of random decisions forests, principal component analysis (PCA) clustering, k-means clustering, support vector machine (SVM), partial-least squares, neural network, Naïve Bayes classifier, linear discriminant analysis, quadratic discriminant analysis, gradient boosting, boosted trees, decision trees, and the like.

Alternatively or optionally, the method may comprise determining an efficacy of the chemical additives to mitigate one or more of the determined wax risks. In some aspects, determining an efficacy of the chemical additives to mitigate one or more of the determined wax risks comprises determining qualitative and quantitative predictions of pour point depression of the hydrocarbon composition based on analysis of samples of the hydrocarbon composition before and after chemical treatment. The analysis of samples of the hydrocarbon composition before and after chemical treatment may comprise performing infrared (IR) fingerprint analysis of the samples before and after chemical treatment. One or more chemical additive efficacy predictive models can be developed based on the IR fingerprint analysis of the samples before and after chemical treatment to predict the efficacy of the chemical additives to mitigate one or more of the determined wax risks. For example, the one or more chemical additive efficacy predictive models are developed using one or more chemical additive efficacy machine learning algorithms. The one or more chemical additive efficacy machine learning algorithms may include principal component analysis (PCA), linear regression, and the like.

Alternatively or optionally, analyzing the sample of the hydrocarbon composition to determine one or more attributes of the sample of the hydrocarbon composition may comprise performing one or more of fingerprint analysis of the sample, high temperature gas chromatography (HTGC) analysis of the sample, differential scanning calorimetry analysis, inductively coupled plasma mass spectrum analysis, combination of the variable analysis, and the like to the sample to determine one or more attributes of the sample.

The fingerprint analysis may comprise using spectroscopy. The spectroscopy may comprise one or more of infrared (IR) spectroscopy, temperature-dependent IR spectroscopy, two-dimensional (2D) spectroscopy, ultra-violet (UV) spectroscopy, near-infrared spectroscopy, mid-infrared spectroscopy, nuclear magnetic resonance spectroscopy, and the like. The one or more attributes of the hydrocarbon composition may include Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), Pour Point (PP), and the like. In some aspects, the one or more of the Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), Pour Point (PP), and the like are predicted based on one or more measured attributes of the sample of the hydrocarbon composition. The attributes may be measured using microscopy, UV-vis spectroscopy, light scattering, acoustic resonance, and the like. In some aspects, the fingerprint analysis is performed at a temperature less than a Wax Appearance Temperature (WAT) of the hydrocarbon composition.

Alternatively or optionally, the one or more predictive models of the hydrocarbon production, transportation, refining, refined hydrocarbon production, processing, handling, storage, and use are developed using one or more machine learning algorithms. The one or more machine learning algorithms may include principal component analysis (PCA), linear regression, logistic regression, and the like.

The wax risks determined by the method may include one or more of wax content, heavy wax content, Wax Appearance Temperature (WAT), Pour Point (PP), wax deposition potential, and the like.

According to the method, mitigating one or more of the determined wax risks may comprise modifying the production, transportation, storage, processing, and/or distribution of the hydrocarbon composition to reduce the determined wax risks.

Also disclosed and described herein are embodiments of a method of reducing wax risks in a hydrocarbon composition comprising obtaining a sample of the hydrocarbon composition; determining one or more wax risks by: analyzing the sample of the hydrocarbon composition to determine one or more attributes of the sample of the hydrocarbon composition; developing one or more predictive models for the hydrocarbon composition based on the analysis of the sample of the hydrocarbon composition; and determining the one or more wax risks based on the developed one or more predictive models; and modifying the production, transportation, storage, processing, and/or distribution of the hydrocarbon composition to reduce the wax risks.

Alternatively or optionally the method may comprise developing a pipe flow model for a pipeline and determining wax risks in the pipeline based on the determined wax risks. In some aspects, developing the pipe flow model for the pipeline comprises using parameters and operating conditions of the pipeline when developing the pipe flow model. The parameters and operating conditions of the pipeline may comprise real-time parameters and operating conditions of the pipeline. Alternatively or optionally, the parameters and operating conditions of the pipeline comprise historical parameters and operating conditions of the pipeline.

In some instances of the method, the modification of the production, transportation, storage, processing, and/or distribution of the hydrocarbon composition comprises determining one or more chemical additives to combine with the hydrocarbon composition to mitigate one or more of the determined wax risks. For example, the one or more chemical additives include one or more wetting agents, emulsion breakers, detergents, dispersants, stabilizers, corrosion inhibitors, sulphide or metal-sulphide dissolvers, polymerization inhibitors, antioxidants, metal deactivators, combinations thereof, and the like. Determining chemical additives to mitigate one or more of the determined wax risks may comprise selecting one or more chemical additives based on matching precipitation characteristics between the one or more chemical additives and wax in the hydrocarbon composition. In some instances, a blend of chemical additives may be determined to mitigate one or more of the determined wax risks. The blend of chemical additives may be determined based on matching precipitation characteristics between the blend of chemical additives and wax in the hydrocarbon composition. The wax in the hydrocarbon composition may be determined based on the analysis of the sample of the hydrocarbon composition to determine the one or more attributes of the sample of the hydrocarbon composition.

In some instances, determining one or more chemical additives to mitigate the determined wax risks may comprise developing qualitative chemical additive predictive models for selecting one or more chemical additives based on the analysis of the sample of the hydrocarbon composition to determine the one or more attributes of the sample of the hydrocarbon composition. The qualitative chemical additive predictive models may be developed using a chemical additive machine learning algorithm such as one or more of random decisions forests, principal component analysis (PCA) clustering, k-means clustering, support vector machine (SVM), partial-least squares, neural network, Naïve Bayes classifier, linear discriminant analysis, quadratic discriminant analysis, gradient boosting, boosted trees, decision trees, and the like.

In some instances, modification of the production, transportation, storage, processing, and/or distribution of the hydrocarbon composition may comprise adding the one or more chemical additives to the hydrocarbon composition in an incoming transport system or crude storage tanks, to a hydrocarbon storage tank farm that holds the crude oil entering the process of hydrocarbon production, transportation, refining, refined hydrocarbon production, processing, handling, storage, and use, to a water wash, to a de-salter, to a hot preheat train after desalting of the refining process, or combinations thereof.

In some instances, the method may further comprise determining an efficacy of the chemical additives to mitigate one or more of the determined wax risks. In some instances, determining an efficacy of the chemical additives to mitigate one or more of the determined wax risks comprises determining qualitative and quantitative predictions of pour point depression of the hydrocarbon composition based on analysis of samples of the hydrocarbon composition before and after chemical treatment. The analysis of samples of the hydrocarbon composition before and after chemical treatment comprises performing infrared (IR) fingerprint analysis of the samples before and after chemical treatment. In some instances the IR fingerprint analysis of the samples before and after chemical treatment can be used to develop one or more chemical additive efficacy predictive models to predict the efficacy of the chemical additives to mitigate one or more of the determined wax risks. The one or more chemical additive efficacy predictive models may be developed using one or more chemical additive efficacy machine learning algorithms including, for example, principal component analysis (PCA), linear regression, and the like.

Optionally or alternatively, analyzing the sample of the hydrocarbon composition to determine one or more attributes of the sample of the hydrocarbon composition may comprise performing one or more of fingerprint analysis of the sample, high temperature gas chromatography (HTGC) analysis of the sample, differential scanning calorimetry analysis, inductively coupled plasma mass spectrum analysis, combination of the variable analysis of the sample, and the like to determine one or more attributes of the sample. In some instances, the fingerprint analysis comprises using spectroscopy, which may include one or more of infrared (IR) spectroscopy, temperature-dependent IR spectroscopy, two-dimensional (2D) spectroscopy, ultra-violet (UV) spectroscopy, near-infrared spectroscopy, mid-infrared spectroscopy, nuclear magnetic resonance spectroscopy, and the like. The determined one or more attributes of the sample of the hydrocarbon composition may comprise Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), Pour Point (PP), and the like. In some instances, one or more of the Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP) are predicted based on one or more measured attributes of the sample of the hydrocarbon composition. Attributes may be measured using microscopy, UV-vis spectroscopy, light scattering, acoustic resonance, and the like. In some instances, the fingerprint analysis is performed at a temperature less than a Wax Appearance Temperature (WAT) for the hydrocarbon composition.

Alternatively or optionally, the one or more predictive models of the hydrocarbon refining may be developed using one or more machine learning algorithms such as principal component analysis (PCA), linear regression, logistic regression, and the like.

The wax risks determined by the method may include one or more of Wax Appearance Temperature (WAT), Pour Point (PP), wax content, heavy wax content, wax deposition potential, and the like. Developing one or more predictive models for the hydrocarbon composition comprises developing on or more predictive models for production, transportation, refining, refined hydrocarbon production, processing, handling, storage, use for the hydrocarbon composition; one or more predictive models for the hydrocarbon composition entering a process of hydrocarbon production, transportation, refining, refined hydrocarbon production, processing, handling, storage, and use; or one or more predictive models for the hydrocarbon composition as the hydrocarbon composition moves through the process of hydrocarbon production, transportation, refining, refined hydrocarbon production, processing, handling, storage, and use; each predictive model based on the analysis of the sample of the hydrocarbon composition.

Further disclosed and described herein are embodiments of a system for using predictive analytics in management of a hydrocarbon process. On one aspect the system comprises a memory, wherein the memory stores computer-readable instructions; and a processor communicatively coupled with the memory, wherein the processor executes the computer-readable instructions stored on the memory, the computer-readable instructions causing the processor to: receive an analysis of a hydrocarbon sample, develop one or more predictive models for a hydrocarbon based on one or more attributes of the sample of the hydrocarbon composition determined in the analysis of the hydrocarbon sample; determine wax risks based on the developed one or more predictive models; and control aspects of the hydrocarbon process based on the determined wax risks to mitigate one or more of the determined wax risks, wherein the analysis is obtained by the following steps: obtaining a sample of the hydrocarbon composition; and analyzing the sample of the hydrocarbon composition to determine the one or more attributes of the sample of the hydrocarbon composition.

Alternatively or optionally, the system may comprise causing the processor to execute instructions to develop a pipe flow model for a pipeline and determine wax risks in the pipeline based on the determined wax risks. In some instances, developing the pipe flow model for the pipeline comprises causing the processor to execute instructions to receive and use parameters and operating conditions of the pipeline when developing the pipe flow model. The parameters and operating conditions of the pipeline may be received by the processor in real-time, and/or historical parameters and operating conditions of the pipeline may be retrieved from the memory and supplied to the processor.

Alternatively or optionally, managing aspects of the hydrocarbon process comprises causing the processor to execute instructions to determine one or more chemical additives to combine with the hydrocarbon composition to mitigate the determined wax risks. The one or more chemical additives may include one or more wetting agents, emulsion breakers, detergents, dispersants, stabilizers, corrosion inhibitors, sulphide or metal-sulphide dissolvers, polymerization inhibitors, antioxidants and metal deactivators or combinations thereof. In some instances the processor determining chemical additives to mitigate the determined wax risks comprises causing the processor to execute instructions to select one or more chemical additives based on matching precipitation characteristics between the one or more chemical additives and wax in the hydrocarbon composition. In some instances, the processor executes instructions to determine a blend of chemical additives to mitigate the determined wax risk. The blend of chemical additives may be determined based on causing the processor to execute instructions to match precipitation characteristics between the blend of chemical additives and wax in the hydrocarbon composition. In some instances, the wax in the hydrocarbon composition is determined by the processor based on the received analysis of the sample of the hydrocarbon composition.

Alternately or optionally, causing the processor to execute instructions to determine one or more chemical additives to mitigate the determined wax risks comprises causing the processor to execute instructions to develop qualitative chemical additive predictive models for selecting one or more chemical additives based on the received analysis of the sample of the hydrocarbon composition. In some instances, the qualitative chemical additive predictive models are developed by the processor executing instructions that comprise one or more chemical additive machine learning algorithms. The chemical additive machine learning algorithm may include one or more of random decisions forests, principal component analysis (PCA) clustering, k-means clustering, support vector machine (SVM), partial-least squares, neural network, Naïve Bayes classifier, linear discriminant analysis, quadratic discriminant analysis, gradient boosting, boosted trees, decision trees, and the like.

Alternately or optionally, controlling aspects of the hydrocarbon process comprises causing the processor to execute instructions to add the one or more chemical additives to the hydrocarbon composition.

In some instances, the system causing the processor to execute instructions to determine an efficacy of the chemical additives to mitigate the determined wax risks. This may comprise causing the processor to execute instructions to determine qualitative and quantitative predictions of pour point depression of the hydrocarbon composition based on analysis of samples of the hydrocarbon composition before and after chemical treatment. In some instances, the analysis of samples of the hydrocarbon composition before and after chemical treatment comprises causing the processor to execute instructions to perform infrared (IR) fingerprint analysis of the samples before and after chemical treatment. In some instances, the processor may be caused to execute instructions to develop one or more chemical additive efficacy predictive models based on the IR fingerprint analysis of the samples before and after chemical treatment to predict the efficacy of the chemical additives to mitigate the determined wax risks. The one or more chemical additive efficacy predictive models are developed by the processer executing instructions that comprise one or more chemical additive efficacy machine learning algorithms. The one or more chemical additive efficacy machine learning algorithms include causing the processor to execute instructions to perform principal component analysis (PCA), linear regression analysis, and the like.

Alternatively or optionally, analyzing the sample of the hydrocarbon composition to determine one or more attributes of the sample of the hydrocarbon composition may comprise performing one or more of fingerprint analysis of the sample, high temperature gas chromatography (HTGC) analysis of the sample, differential scanning calorimetry analysis, inductively coupled plasma mass spectrum analysis, combination of the variable analysis of the sample, and the like to determine one or more attributes of the sample. In some instances, the fingerprint analysis comprises using spectroscopy. The spectroscopy may comprise one or more of infrared (IR) spectroscopy, temperature-dependent IR spectroscopy, two-dimensional (2D) spectroscopy, ultra-violet (UV) spectroscopy, near-infrared spectroscopy, mid-infrared spectroscopy, nuclear magnetic resonance spectroscopy, and the like. The one or more attributes may include Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), Pour Point (PP), and the like. In some instances, one or more of the Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP) are predicted based on one or more measured attributes of the sample of the hydrocarbon composition. The attributes can be measured using microscopy, UV-vis spectroscopy, light scattering, acoustic resonance, and the like.

Alternately or optionally, the fingerprint analysis may be performed at a temperature less than a Wax Appearance Temperature (WAT) of the hydrocarbon composition.

Alternately or optionally, the one or more predictive models of the hydrocarbon refining can be developed by the processor executing instructions that comprise one or more machine learning algorithms. The one or more machine learning algorithms can include principal component analysis (PCA), linear regression, logistic regression, and the like.

In some instances, causing the processor to execute instructions to determine wax risks comprises determining one or more of Wax Appearance Temperature (WAT), Pour Point (PP), wax content, heavy wax content, wax deposition potential, and the like.

In some instances, the system controlling aspects of the hydrocarbon process based on the determined wax risks to mitigate one or more of the determined wax risks comprises controlling one or more of hydrocarbon production, transportation, refining, refined hydrocarbon production, processing, handling, storage, and use as the hydrocarbon composition enters the production, transportation, refining, refined hydrocarbon production, processing, handling, storage, and use or moves through the production, transportation, refining, refined hydrocarbon production, processing, handling, storage, and use Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

DRAWINGS

The accompanying drawings, which are incorporated in and constitute a part of this specification, illustrate embodiments and together with the description, serve to explain the principles of the methods and systems:

Figure 5:
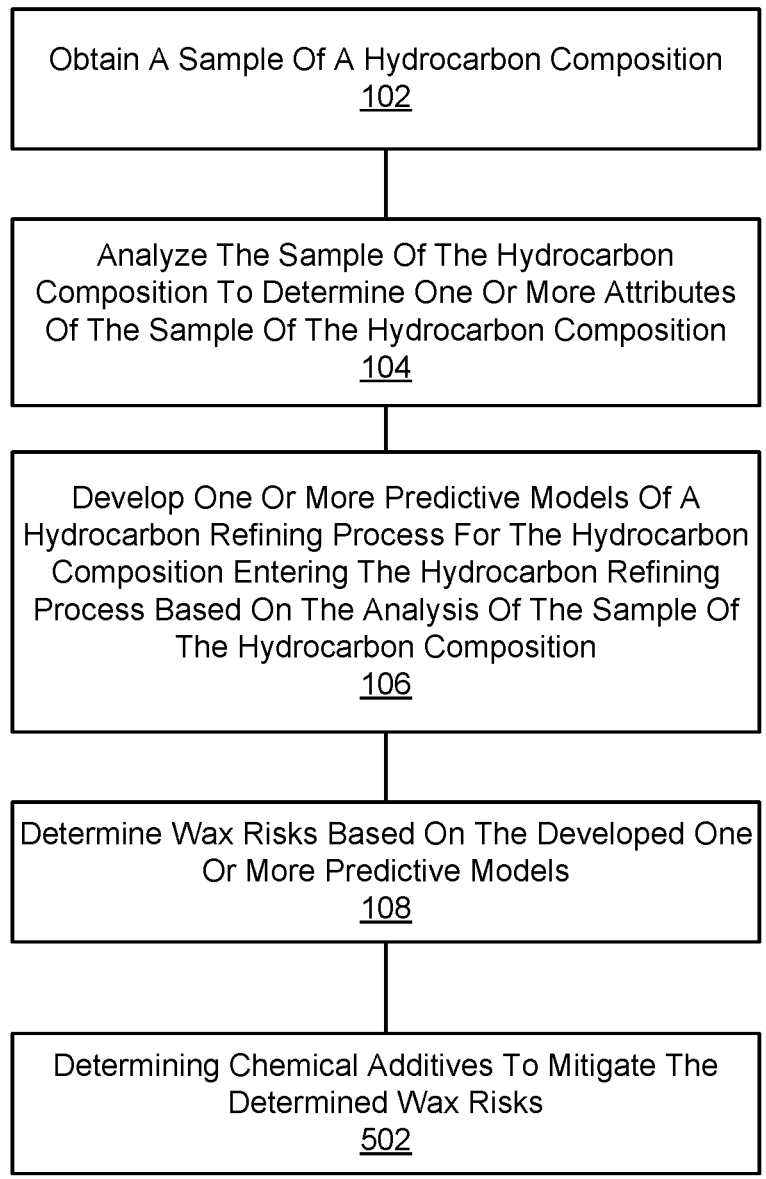
Figures 6A, 6B:
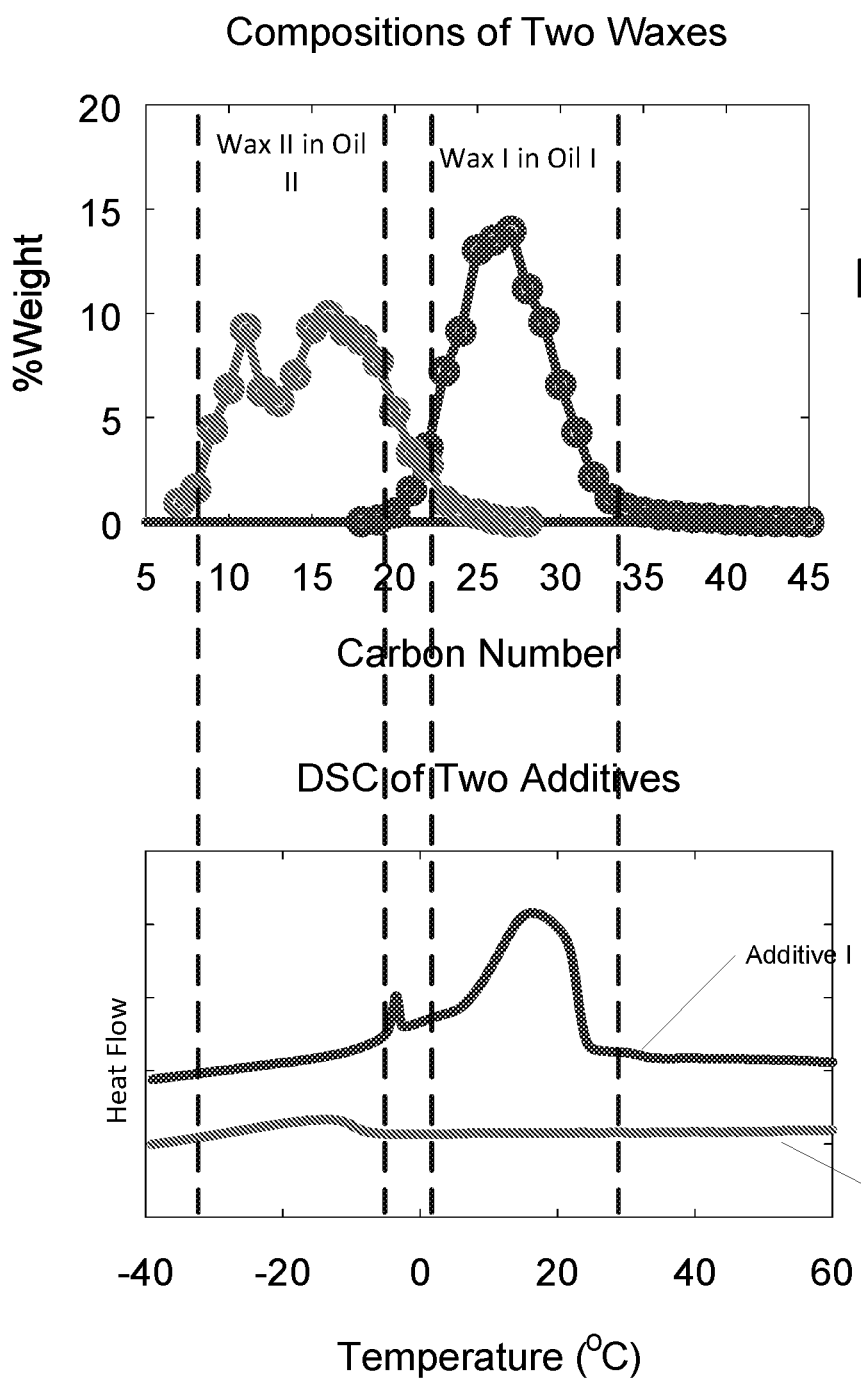
Figure 6C:
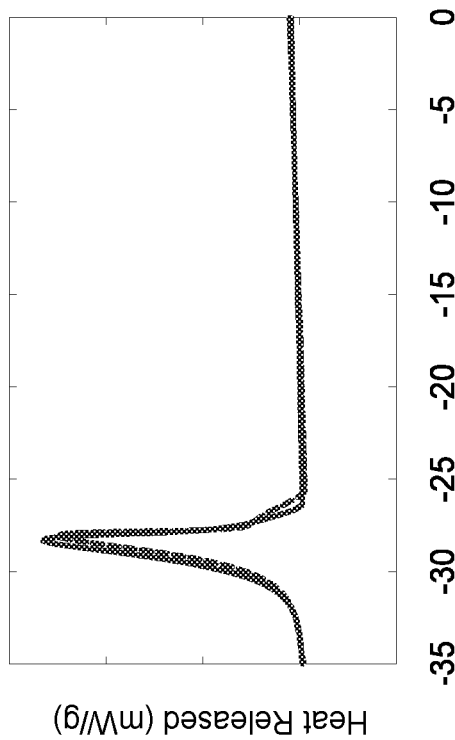
Figure 6D:
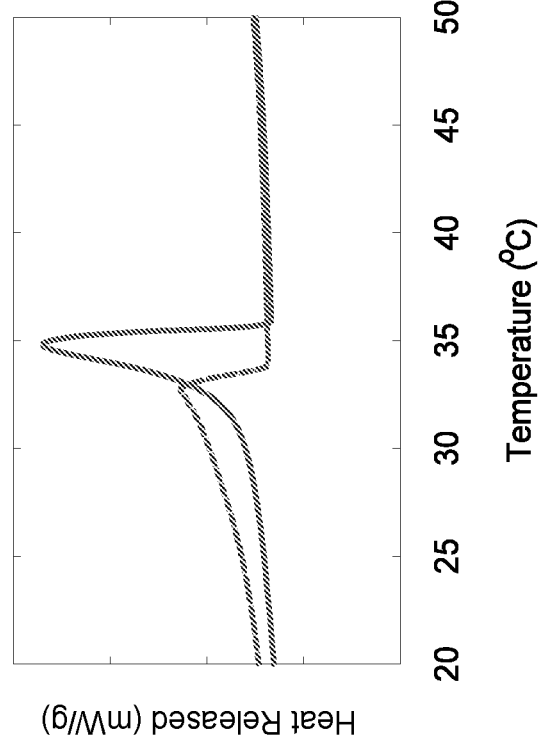
Figure 7:
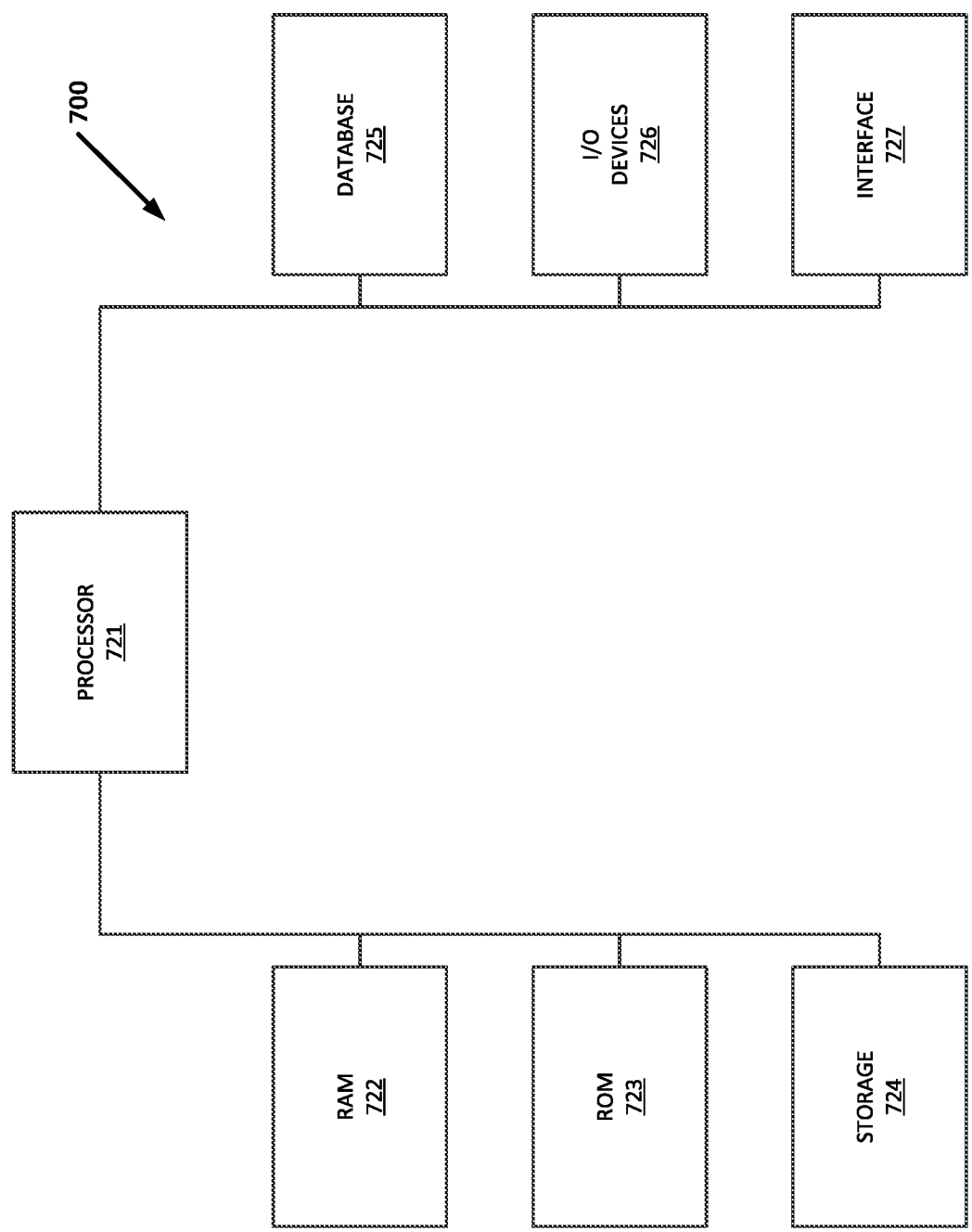

FIG. 5 is a flowchart illustrating yet another exemplary alternative method of determining wax risk and way of mitigating of a hydrocarbon composition; and FIGS. 6A and 6B are a graphic representation of matching precipitation characteristics between additives and waxes to determine chemical additives or chemical additive blends to enhance performance of the hydrocarbon composition in hydrocarbon production, transportation, refining, refined hydrocarbon production, processing, handling, storage, and use;

FIGS. 6C and 6D illustrate the assessment of potential chemical additive efficacy based on the variation in the wax precipitation characteristics upon chemical treatment characterized by Differential Scanning calorimetry (DSC); and FIG. 7 illustrates an exemplary computer that can be used for analyzing the sample of the hydrocarbon composition to determine one or more attributes of the sample of the hydrocarbon composition; developing one or more predictive models of hydrocarbon production, transportation, refining, refined hydrocarbon production, processing, handling, storage, and use for the hydrocarbon composition of interest based on the analysis of the sample of the hydrocarbon composition; and determining wax risks based on the developed one or more predictive models.

DETAILED DESCRIPTION

Before the present methods and systems are disclosed and described, it is to be understood that the methods and systems are not limited to specific methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As used herein, the term "fouling" refers to the accumulation of a phase separate from the mobile phase on the surfaces of the equipment in hydrocarbon production, transportation, refining, refined hydrocarbon production, processing, handling, storage, and use. For instance, non-gaseous material can separate from a gaseous mobile phase and non-liquid material can separate from a liquid mobile phase. The separated phase reduces the space through which the hydrocarbon can pass, and reduces the contact between the hydrocarbon and heat exchanger surfaces.

As used herein, the term "hydrocarbon," "hydrocarbon composition" or "hydrocarbon sample" refers to crude oil, crude oil blends, tower bottoms, gas oil/diesel fuel, naphtha, condensates, slop oil, hydrotreated oil, hydrocracked oil, and mixtures thereof.

Provided herein are methods to evaluate the wax risks of a given hydrocarbon sample. With an understanding of the potential wax risks, an oil producer or refiner can take steps to mitigate the risks. Because the methods disclosed herein provide a previously unavailable level of detail regarding specific risk mechanisms, the oil producer or refiner can readily select the appropriate mitigation steps to maximize the efficiency of the oil production, transportation, refining, refined hydrocarbon production, processing, handling, storage, and use. Wax risks of a crude oil or a blend in oil production and transportation include the tendency to deposit materials on the surface of oil production/transportation equipment, including wellbore tubing, pipelines, etc., leading to decreased cross-sectional area available for oil flow, increased pump power to maintain flow and even risk of clogging. Wax risks in refining processes include the tendency to deposit materials on the heat transfer surface, leading to decrease in heat transfer efficiency. Heat exchanger network systems are used to recover as much sensible heat as possible from process streams around the crude distillation unit (CDU) by preheating the feedstock prior to entering the furnace. The more the heat transferred to the feed in the exchangers, the less energy/fuel is required to heat the crude to the required distillation temperature range. The hottest exchangers have a direct impact on the furnace inlet temperature. Exchangers with the highest heat flux or low flow velocity usually show the highest fouling rates.

Fouling is caused by the precipitation of materials, both organic and inorganic and including wax, present in the feed or formed during the cooling of the hydrocarbon stream. To assist oil producers/refiners to optimize crude blends and minimize the fouling potential in wellbore tubing, oil transportation pipeline, crude preheat exchangers and other refinery equipment caused by wax, a more proactive and predictive approach to estimate wax risks is a significant industry need. The fouling potential can be expressed in more than one way, such as the loss of heat transfer (delta T, or $\Delta T$), increase of pressure drop (delta P, or $\Delta P$) or amount of foulant (e.g., thickness of solids, volume of foulant, or weight of foulant), since all three can reflect the amount of fouling occurring on solid surfaces in of tubing, pipeline and other production or refinery equipment. Determining wax risks and mitigating them can lower fouling potential. Determined wax risks may include one or more of wax appearance temperature (WAT), pour point (PP), wax deposition potential, and the like. Additional details regarding fouling in a refining process can be found in Patent Cooperation Treat application PCT/US16/65232 filed Dec. 7, 2016, which is fully incorporated by reference.

Figure 1:
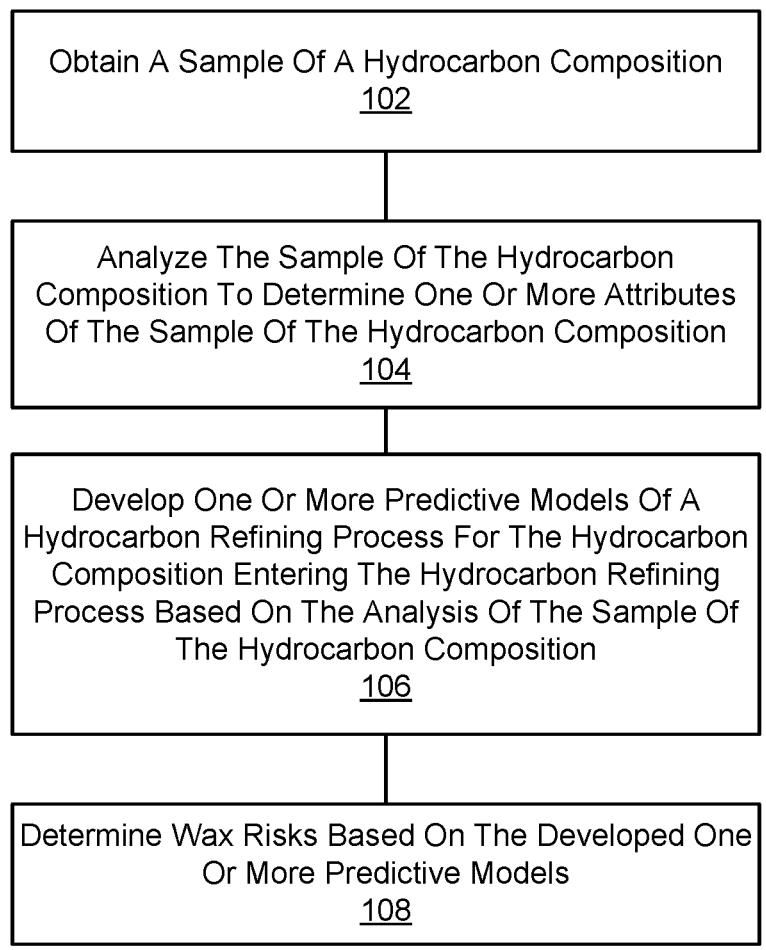
FIG. 1 is a flowchart illustrating an exemplary method of determining wax risk and ways of mitigating of the wax risk associated with the hydrocarbon composition.

FIG. 1 is a flowchart illustrating an exemplary method of determining wax risk and way of mitigating of a hydrocarbon composition. In certain selected embodiments, wax risks can be evaluated by measuring and/or analyzing a hydrocarbon sample and/or various portions thereof. The exemplary method begins by 102 obtaining a sample of the hydrocarbon composition. Generally, this sample is taken at any point of the oil production/transportation, refining, refined hydrocarbon production, processing, handling, storage, and use. For example, the sample may be obtained from storage tanks that store the hydrocarbon composition prior to refining. Obtaining the sample may be a manual process, or it may involve automated mechanisms for obtaining the sample. The sample can be of any size. Advantageously, embodiments as disclosed herein require only a small sample size. For example, the sample size may be 50 mL or less for the embodiments disclosed herein.

At 104, the obtained sample of the hydrocarbon composition is analyzed to determine one or more attributes of the sample. Analyzing the sample of the hydrocarbon composition to determine one or more attributes of the sample of the hydrocarbon composition comprises performing one or more of a fingerprint analysis of the sample, a high temperature gas chromatography (HTGC) analysis of the sample, differential scanning calorimetry analysis, inductively coupled plasma mass spectrum analysis or combination of the variable analysis of the sample to determine one or more attributes of the sample. If fingerprint analysis of the sample is performed, it may involve the use of spectroscopy. If spectroscopy is used, it may comprise one or more of infrared (IR) spectroscopy, near-infrared spectroscopy, nuclear magnetic resonance spectroscopy temperature-dependent IR spectroscopy, two-dimension (2D) IR, UV (ultraviolet) spectroscopy, mid-IR spectroscopy, and the like.

As noted, the fingerprint analysis can be performed using IR spectroscopy, for instance as described in U.S. Pat. No. 6,087,662, the disclosure of which is hereby fully incorporated by reference. For instance, the fingerprint analysis can be used to measure paraffin/wax related properties such as wax appearance temperature, pour point, paraffin distribution, wax content, heavy wax content, and wax deposition potential, using multiple variable regression analysis, specifically, by:

measuring at least one frequency in the middle infrared absorption in the band of 3800-650 $cm^{-1}$;

taking each of the absorbances measured, or a mathematical function thereof;

performing statistical treatment using the above absorbances or functions as individual independent variables;

assigning and applying weighting constants or their equivalents to said independent variables;

applying the above steps using compositions of known wax/paraffin properties to calibrate the instrument and determine said weighting constants or equivalents;

repeating said steps with unknown compositions, and applying the weighting constants or equivalents determined during said calibration with compositions of known wax/paraffin properties to output a signal or signals indicative of wax/paraffin properties for the unknown compositions.

In one aspect, the fingerprint analysis may be performed at a temperature that is below the Wax Appearance Temperature (WAT) for the hydrocarbon composition under analysis. Generally, when the fingerprint analysis is performed at a temperature that is below the WAT for the hydrocarbon, the accuracy of prediction of WAT and the pour point (PP) is improved. For example, WAT prediction may be improved by as much as ~20° C. and PP prediction may improve as much as ~10° C. by performing fingerprint analysis at a temperature that is below the WAT temperature for the hydrocarbon composition.

The attributes of the hydrocarbon composition, as reflected in the sample by the analysis, can include one or more of a Total Acid Number (TAN), American Petroleum Institute gravity (API gravity), Colloid Instability Index (CII), viscosity, Wax Appearance Temperature (WAT), Pour Point (PP), SG (specific gravity); SARA: Sat (saturates), Aro (aromatic), Res (resin), Asp(asphaltene); viscosity; rheology; wax content, heavy wax content, and the like. In one certain embodiment, the attributes are measured from the sample. In another certain embodiments, only some (less than the total determined attributes) are measured, while other attributes are predicted based on the one or more measured attributes of the sample of the hydrocarbon composition. When the attributes are measured, they may be measured using, for example, microscopy, UV-vis spectroscopy, light scattering, acoustic resonance, and the like.

Combination of the variable analysis comprises any possible mathematic combination of above attributes including ratios, PCAs (principal components/linear combination) etc. The analysis could involve single properties or multi properties, or any combination e.g. ratio, principle components. Principal component analysis (PCA) is a dimensionality reduction technique that was initially adopted to deal with the autocorrelation that exists between multiple crude oil properties (e.g., viscosity, API, density, boiling point, etc.) and identify the most important properties to describe the types of crude oils.

At 106, one or more predictive models of a hydrocarbon production, transportation, refining, refined hydrocarbon production, processing, handling, storage, and use process are developed for the hydrocarbon composition being produced or transported through tubing or pipelines or the hydrocarbon composition entering the hydrocarbon refining process, and refined hydrocarbon products being produced, processed, and used. These one or more models are developed based at least in part on the analysis of the sample of the hydrocarbon composition. The models are developed using machine learning algorithms. Machine learning algorithms cover qualitative modelling (unsupervised clustering0 and quantitative modelling (supervised regression and classification). The machine learning algorithms can include principal component analysis (PCA), linear regression analysis, logistic regression analysis, PCA clustering; k-means clustering; SVM (support vector machine); rf (random forest); partial-least squares; neural network; Naïve Bayes classifier; linear discriminant analysis; quadratic discriminant analysis; gradient boosting; boosted trees; decision trees, and the like. These predictive models are trained by a labelled dataset containing a few crudes properties as inputs, a few wax properties and chemical performance as outputs. Chemical performance could be deposition inhibition rate, chemical performance level (e.g. high, medium, low), chemical recommendation, dosage recommendation, and the like. An example of chemical prediction model training comprises training a classification model using the complete dataset. The model was fitted using overall 167 experimental observations, and 3 classification labels: H, M, and L for four chemicals. It was found that accuracies ranged from ~65-85%. The performance of classification models is generally represented using the confusion matrix, in which the observed classes of the data are tabulated against the classes predicted from the model. The overall accuracy rate can then be used as a performance indicator, which reflects the agreement between the observed and predicted classes.

Figure 2A:
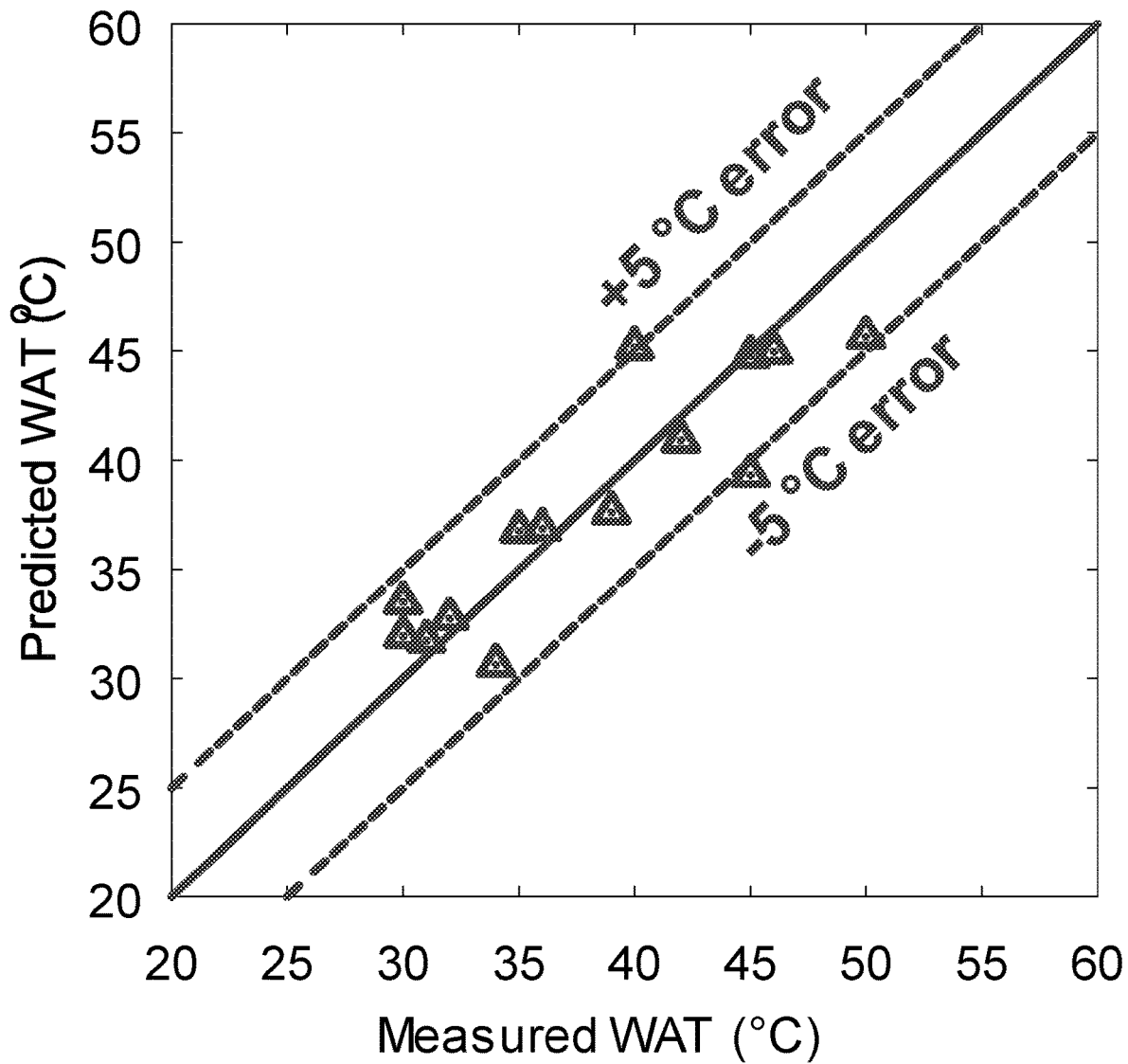
FIG. 2A illustrates a graph showing exemplary results for the ability of the predictive models developed in 106 to predict the WAT of crude oils and refined hydrocarbon fluids.
Figure 2B:
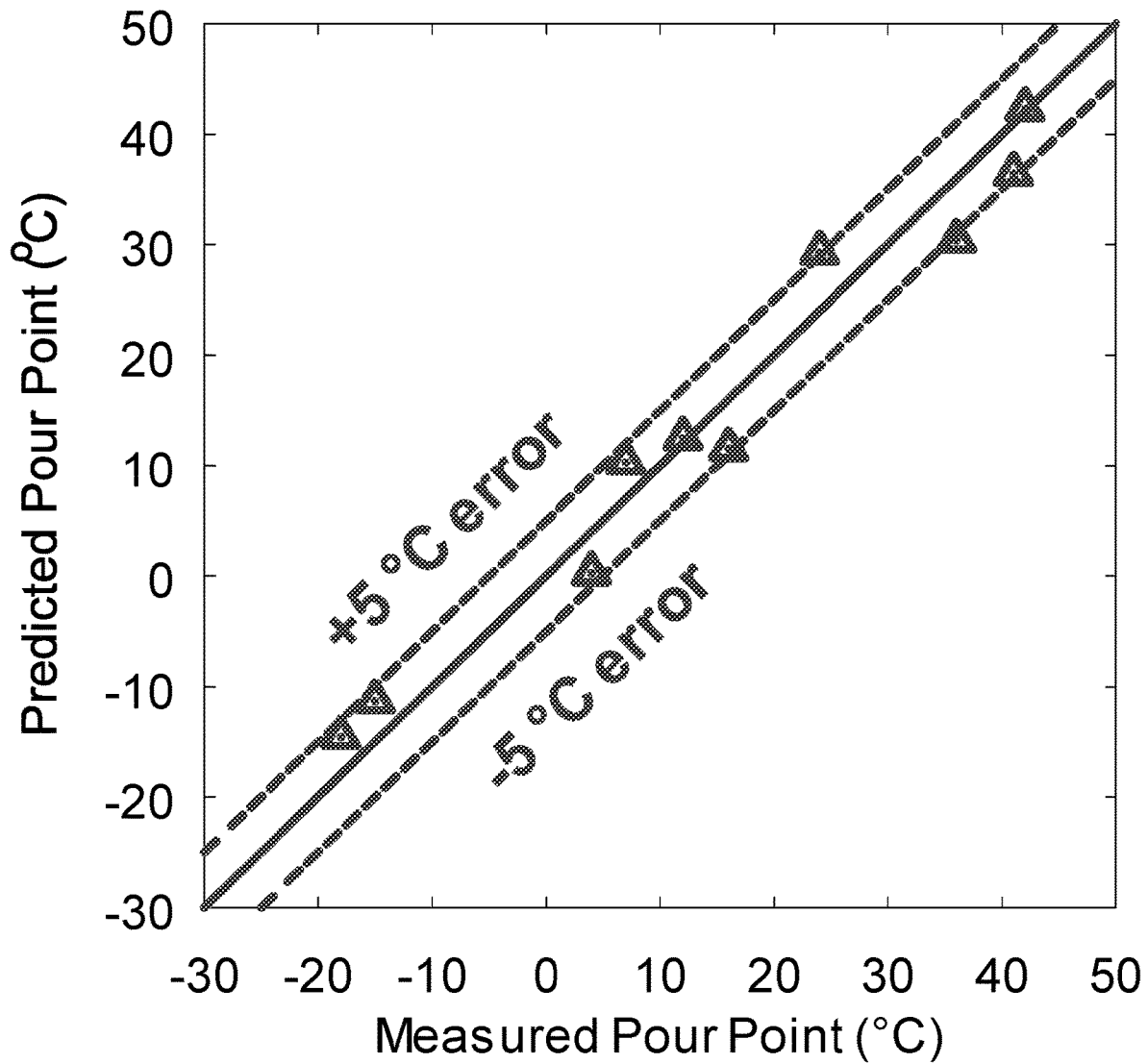
FIG. 2B illustrates a graph showing exemplary results for the ability of the predictive models to predict the PP of crude oils and refined hydrocarbon fluids.
Figure 2C:
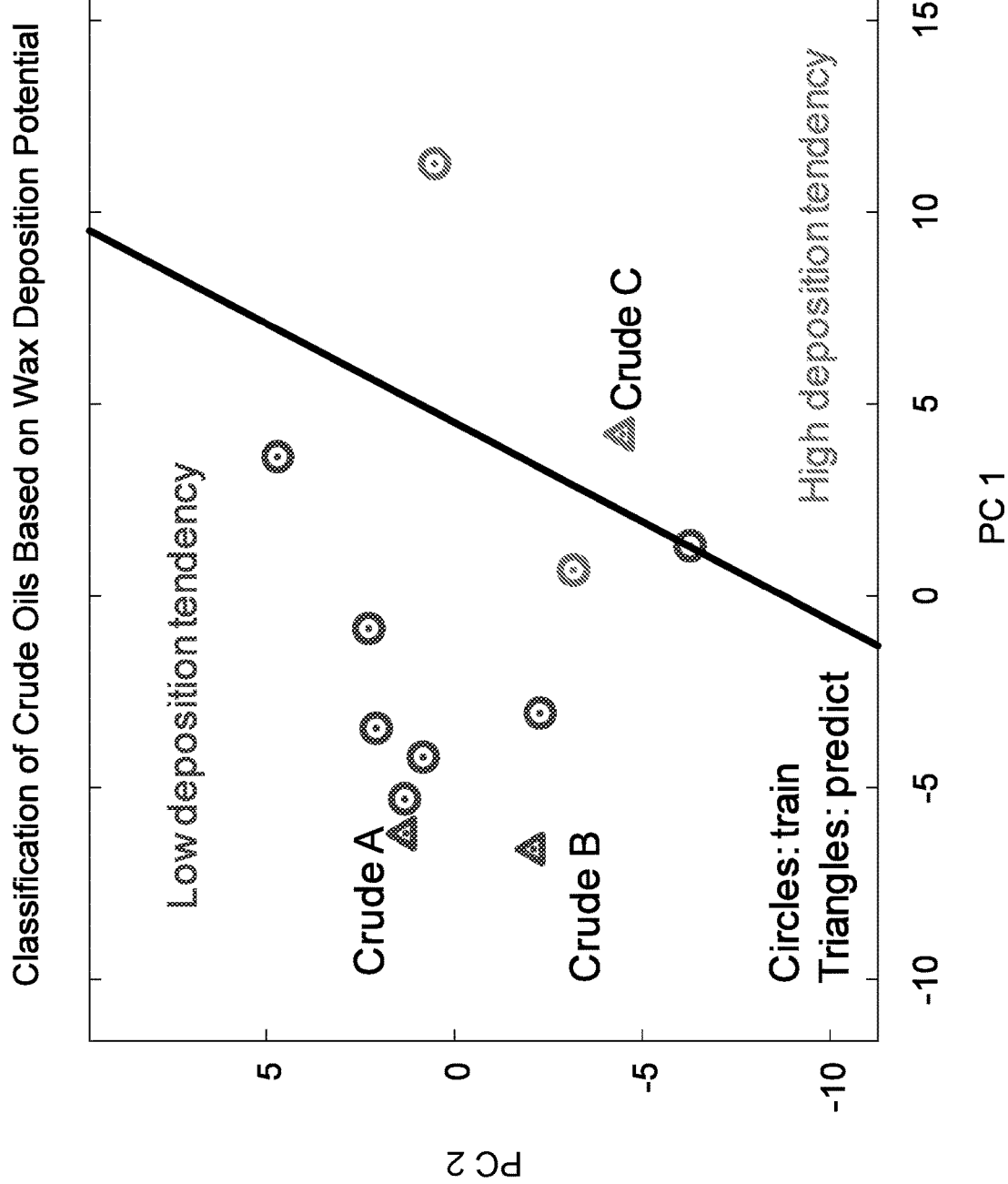
FIG. 2C illustrates a graph showing exemplary results for the ability of the predictive models to predict the wax deposition potential of crude oils and refined hydrocarbon fluids.
Figure 2D:
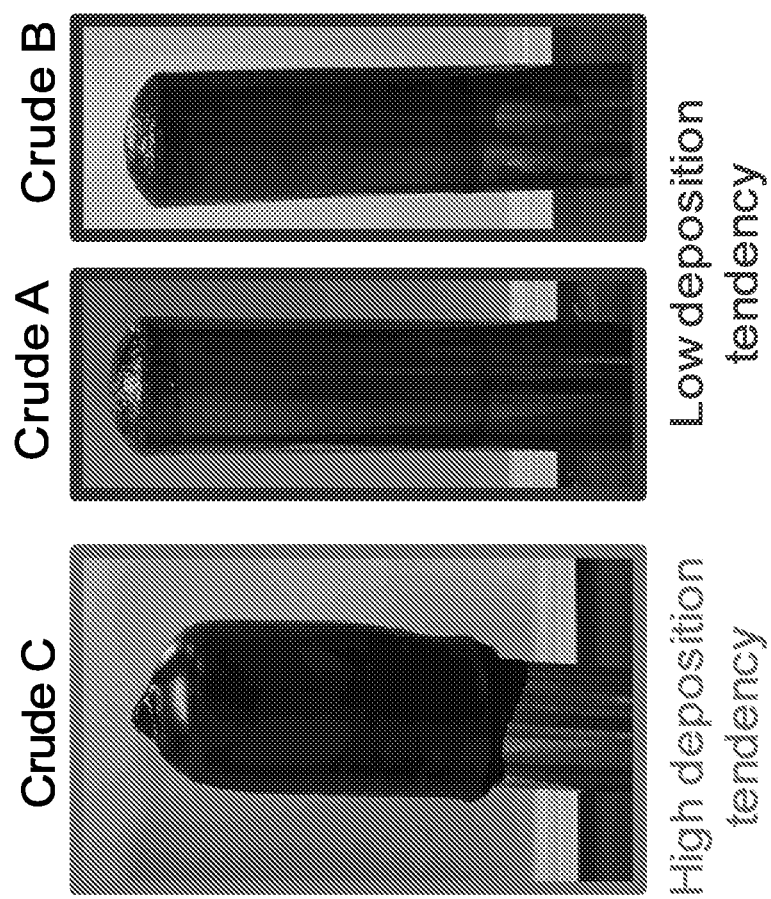
FIG. 2D are images of the three samples of crude oil from FIG. 2C.
Figure 2E:
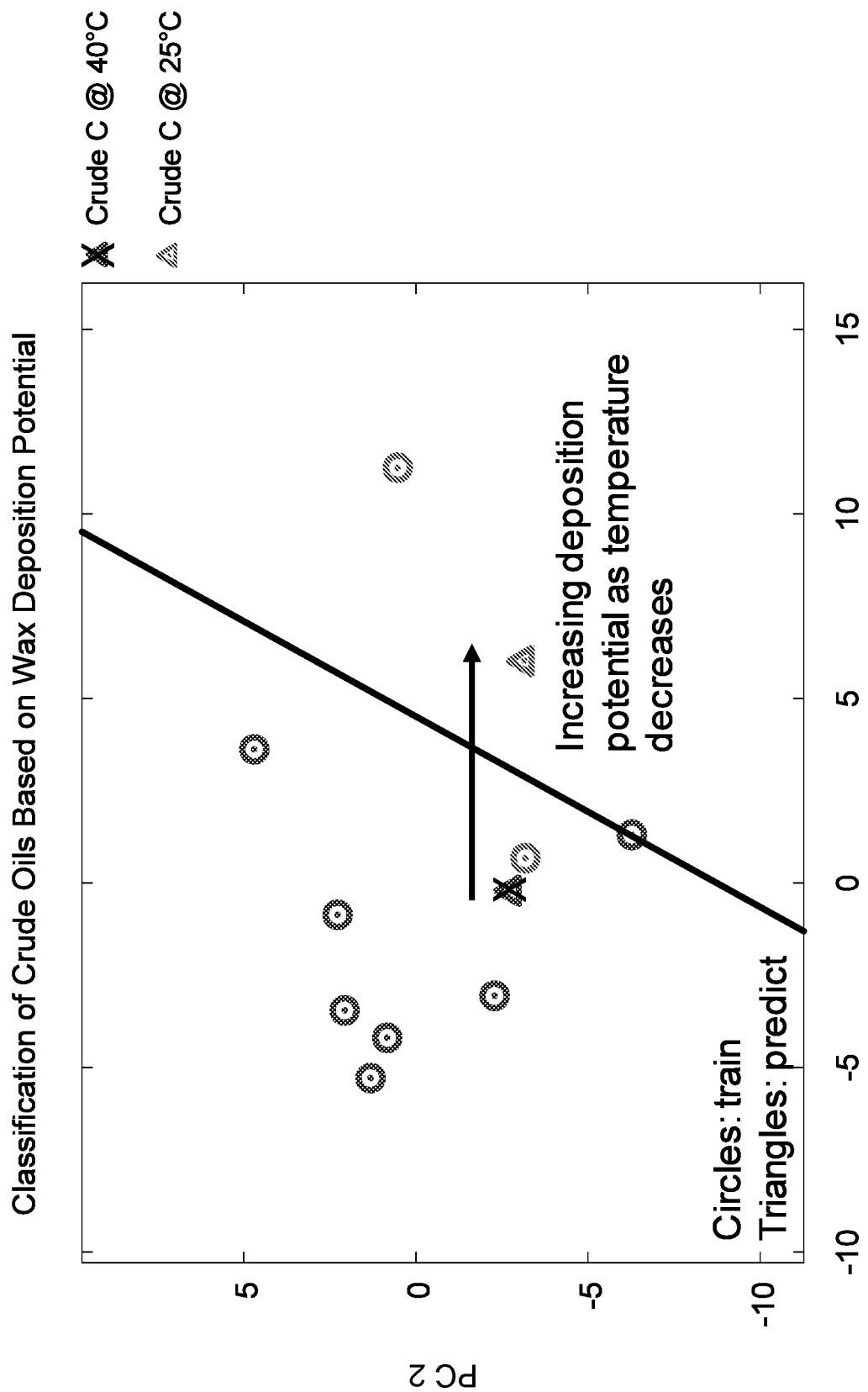
FIG. 2E illustrates prediction of the effect of temperature on wax deposition potential of crude oils and refined hydrocarbon fluids.
Figure 2F:
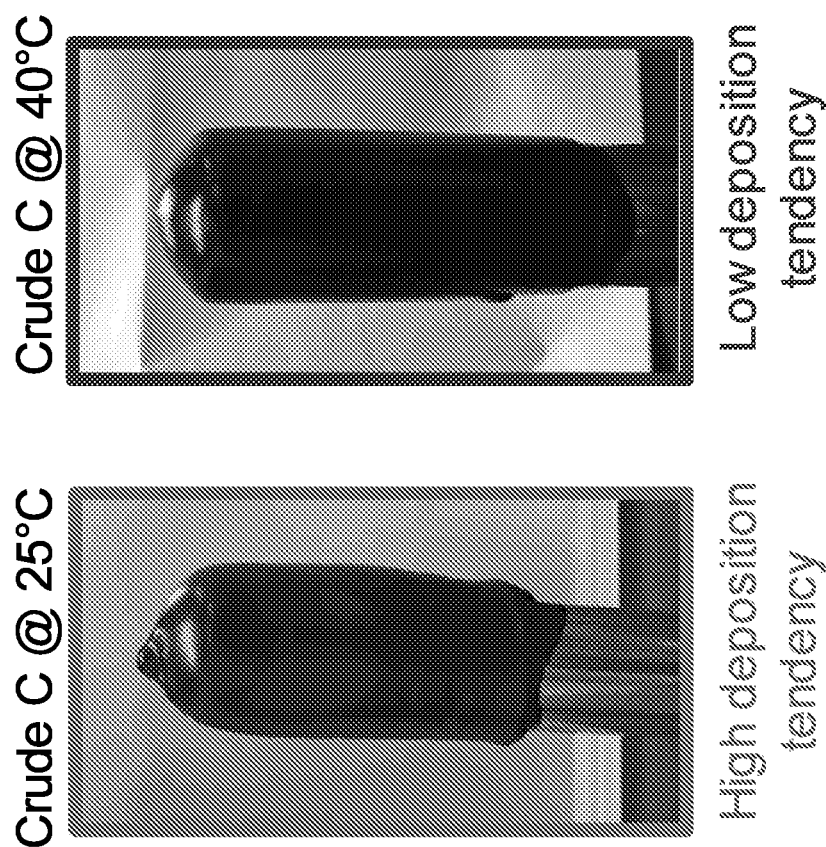
FIG. 2F is an image of the sample in FIG. 2E that shows high tendency deposition at 25 C and low deposition tendency at 40 C.
Figure 2G:
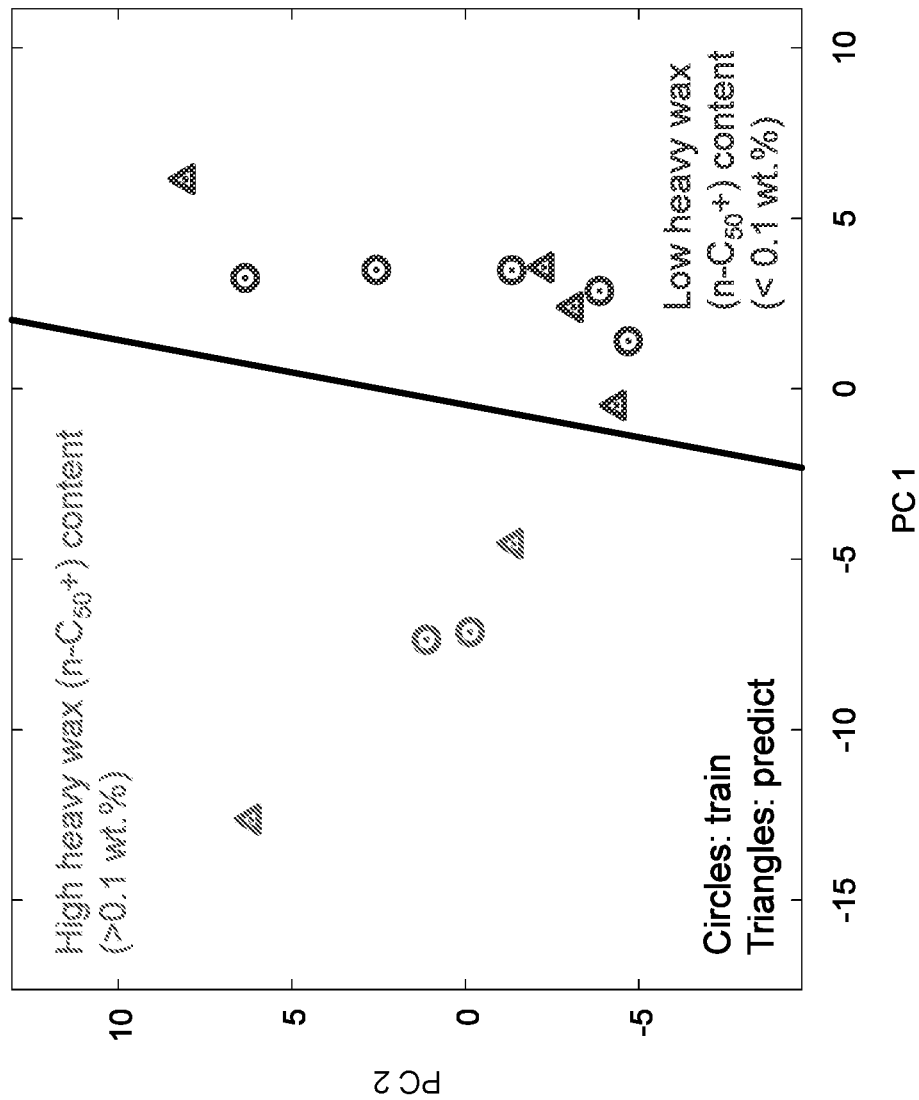
FIG. 2G is a graph that illustrates the exemplary results for the ability of the predicative model to predict the heavy wax content (n-C50+ wax) of oils.

At 108, the wax risks for the hydrocarbon sample are predicted using the developed predictive models developed in 106 based on the analysis of the hydrocarbon sample in 104. Predicting the wax risks may involve predicting one or more of wax appearance temperature (WAT), pour point (PP), wax deposition potential, wax content, heavy wax content, and the like. For example, FIG. 2A illustrates a graph showing exemplary results for the ability of the predictive models developed in 106 to predict the WAT of crude oils and refined hydrocarbon fluids. The exemplary graph shows the measured WAT (x-axis) plotted against the predicted WAT (y-axis). The predicted WAT was predicted by the trained predictive models in 106 based on the results of IR analysis on the hydrocarbon sample performed in 104. The graph shows dashed lines showing absolute errors for +/−5 degree C. FIG. 2B illustrates a graph showing exemplary results for the ability of the predictive models developed in 106 to predict the PP of crude oils and refined hydrocarbon fluids. The exemplary graph shows the measured PP (x-axis) plotted against the predicted PP (y-axis). The predicted PP was by the trained predictive models in 106 based on the results of IR analysis on the hydrocarbon sample performed in 104. The graph shows dashed lines showing absolute errors for +/−5 degree C. FIG. 2C illustrates a graph showing exemplary results for the ability of the predictive models developed in 106 to predict the wax deposition potential of crude oils and refined hydrocarbon fluids. The exemplary graph shows three samples of crude—Crude A, Crude B, and Crude C. Measured values, used for training the predictive models are shown as circles. Predicted values are shown as triangles. High deposition tendency is shown to the right of the diagonal line and low deposition tendency is shown to the left of the diagonal line. FIG. 2D are images of the three samples from FIG. 2C. As can be seen the deposition of the sample with the high deposition tendency is greater than the deposition of the samples with the low deposition tendency. FIG. 2E illustrates prediction of the effect of temperature on wax deposition potential of crude oils and refined hydrocarbon fluids. The exemplary graph shows one sample of Crude C. Measured values, used for training the predictive models are shown as circles. Predicted values are shown as triangles (at different temperatures). High deposition tendency is shown to the right of the diagonal line and low deposition tendency is shown to the left of the diagonal line. As can be seen, the deposition potential increases as temperature decreases. FIG. 2F is an image of the sample in FIG. 2E that shows high tendency deposition at 25 C and low deposition tendency at 40 C. FIG. 2G is a graph that illustrates the exemplary results for the ability of the predicative model to predict the heavy wax content (n-C50+ wax) of oils. The heaviest fraction (n-C50+) of wax contained by oils is the first portion to precipitate upon cooling. As a result, the potential of waxy oils to cause gelation/fouling issues can be characterized by the heavy wax content. As is illustrated by this figure, measured values are represented as circles and predicted values are represented as triangles. The oils located to the right of the solid black line have relatively low heavy wax contents, i.e., <0.1 wt. % while examples shown on the left-side of the black line are with high heavy wax contents, i.e., >0.1 wt. %.

Figure 3:
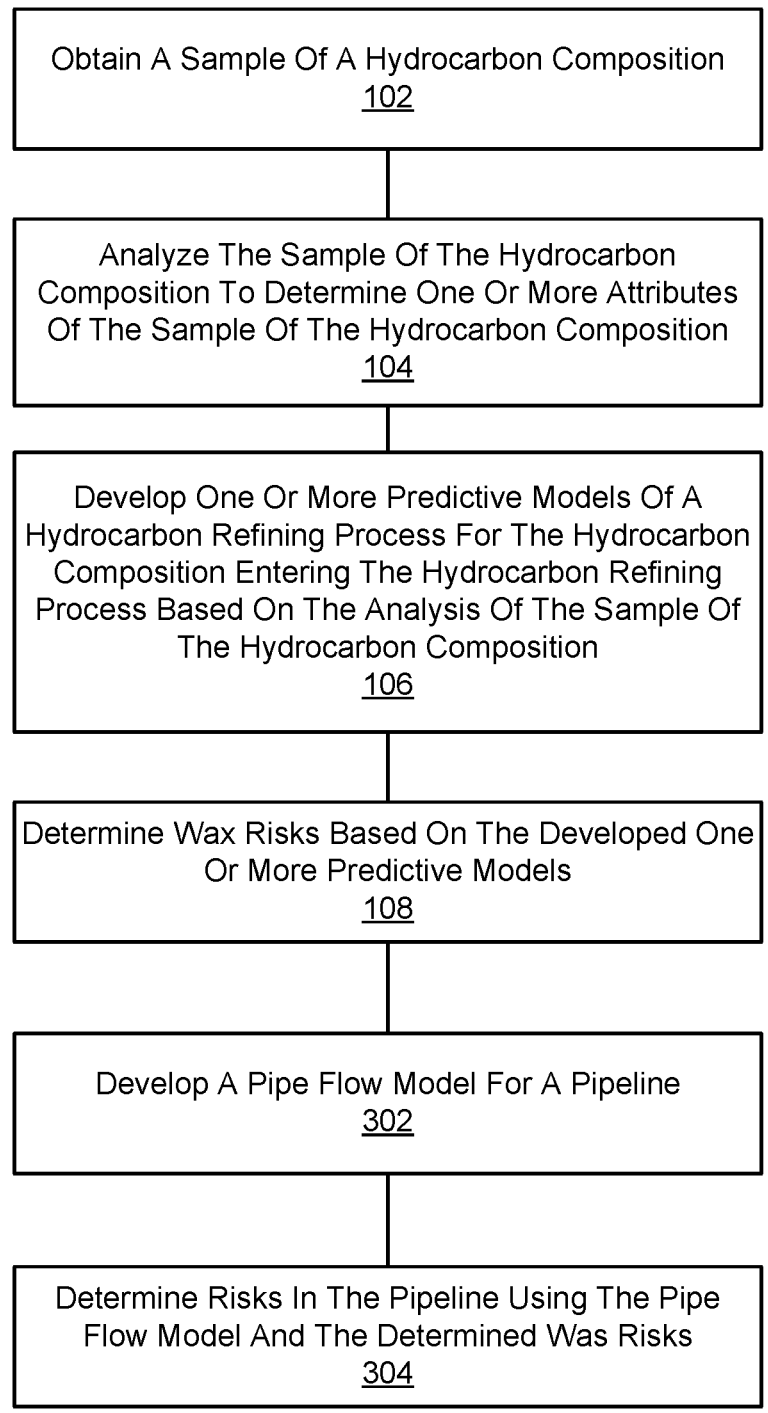
FIG. 3 is a flowchart illustrating an exemplary alternative method of determining wax risk and way of mitigating of a hydrocarbon composition.
Figure 4:
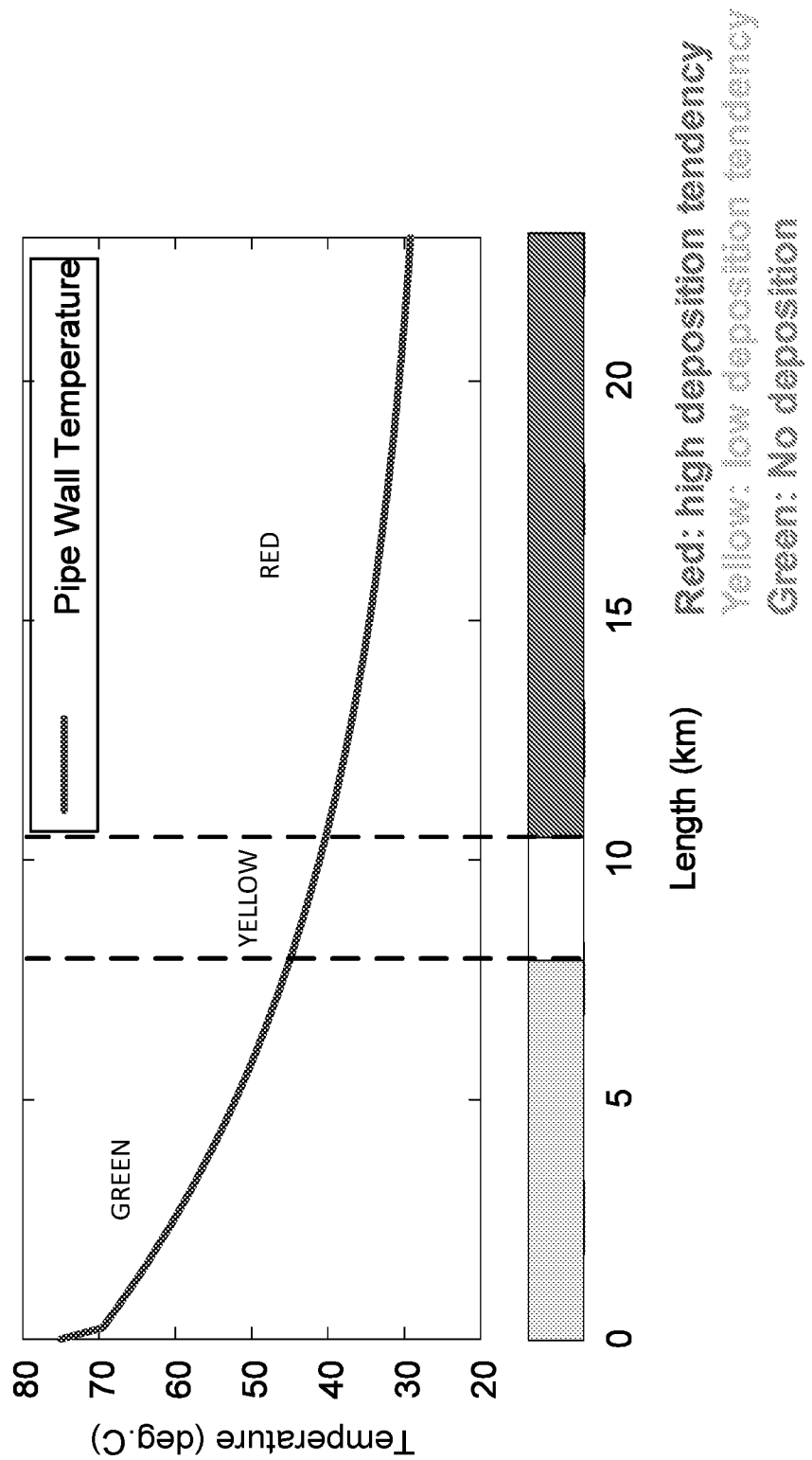
FIG. 4 is an exemplary graph that shows the results of predicting wax deposition in a modelled pipeline based on the wax risks predicted in the disclosed embodiments.

FIG. 3 is a flowchart illustrating an exemplary alternative method of determining wax risk and way of mitigating of a hydrocarbon composition. The embodiments shown in FIG. 3 includes the steps 102-108, as described with reference to FIG. 1. FIG. 3 further includes 302 developing a pipe flow model for a pipeline and 304 determining wax risks in the pipeline based on the pipe flow model and the wax risks determined at 108. Generally, developing the pipe flow model for the pipeline comprises using parameters and operating conditions of the pipeline when developing the pipe flow model. These parameters may comprise, for example, temperatures at different locations along the pipeline, both internal to the pipeline and external (ambient), flow rates, pressures, viscosity, valve positions, and the like. The parameters may be obtained real-time from systems and devices that constantly monitor pipeline conditions, or they may be obtained from logged and/or stored data about the operation of pipeline. In some instances, parameters and operating conditions of the pipeline may comprise a combination of real-time and stored information. FIG. 4 is an exemplary graph that shows the results of predicting wax deposition in a modelled pipeline based on the wax risks predicted in 108. As can be seen, the graph plots temperature (pipe wall temperature) versus length of the pipeline. As the length of the pipeline increase and the temperature of the pipe wall decrease, the wax deposition tendency increases.

FIG. 5 is a flowchart illustrating yet another exemplary alternative method of determining wax risk and way of mitigating of a hydrocarbon composition. The embodiments shown in FIG. 3 includes the steps 102-108, as described with reference to FIG. 1. FIG. 5 further includes the step of 502 determining chemical additives to mitigate the determined wax risks. In one aspect, determining chemical additives to mitigate the determined wax risks comprises selecting one or more chemical additives based on matching precipitation characteristics between the one or more chemical additives and wax in the hydrocarbon composition. Matching precipitation characteristics between additives and waxes generally leads to satisfying performance. For example, as shown in exemplary FIGS. 6A and 6B, based on the precipitation characteristics of the additive, Additive I is likely to interact with Wax I (heavier) and Additive II is likely to interact with Wax II (lighter). As can be seen form the graphs of FIGS. 6A and 6B, Oil I+Additive I=−17 C and Oil II+Additive II ΔPP=−20 C. Additive I+Wax II or Additive II+Wax I are mismatches that result in no efficacy. Mismatches of precipitation characteristics explain the lack of efficacy.

Chemical additives can be applied during production, transportation, storage, processing, and/or distribution of the hydrocarbon composition. The chemical additives can include one or more one or more wetting agents, emulsion breakers, detergents, dispersants, stabilizers, corrosion inhibitors, sulphide or metal-sulphide dissolvers, polymerization inhibitors, antioxidants and metal deactivators or combinations thereof.

In some instances, the additive may comprise a blend of similar class of chemical additives. As with above, the blend of chemical additives for minimizing wax deposition risk can be determined based on matching precipitation characteristics between the blend of chemical additives and wax in the hydrocarbon composition. Table I, below, is an example showing how a blend of two additives results in an optimal pour point:

TABLE I

| | ADDITIVE I DOSAGE | ADDITIVE II DOSAGE | POUR POINT (° F.) |
|---|---|---|---|
| Untreated Oil | 0 | 0 | 55 |
| Treatment Program I | 1000 | 0 | 30 |
| Treatment Program II | 0 | 1000 | 55 |
| Treatment Program III | 500 | 500 | −10 |

As can be seen in Table 1, Treatment Program III results in the lowest pour point, thus it is the optimal chemical additive blend in this example.

When determining chemical additives to add to the hydrocarbon composition, the amount of wax in the hydrocarbon composition can either be measured or predicted, as described above.

In one aspect, determining chemical additives (or chemical additive blends) to mitigate the determined wax risks may comprise developing qualitative chemical additive predictive models for selecting one or more chemical additives based on the analysis of the sample of the hydrocarbon composition to determine the one or more attributes of the sample of the hydrocarbon composition. The qualitative chemical additive predictive models can be developed using a chemical additive machine learning algorithm. For example, the chemical additive machine learning algorithm may include one or more of random decisions forests (i.e. Random Forest™, Salford Systems, San Diego, Calif.), principal component analysis (PCA) clustering, k-means clustering, support vector machine (SVM), partial-least squares, neural network, Naïve Bayes classifier, linear discriminant analysis, quadratic discriminant analysis, gradient boosting, boosted trees, decision trees, and the like.

Though not shown in FIGS. 6A and 6B, one embodiment of the disclosed method may further comprise determining an efficacy of the chemical additives to mitigate the determined wax risks. In one example, determining an efficacy of the chemical additives to mitigate the determined wax risks comprises determining qualitative and quantitative predictions of pour point depression of the hydrocarbon composition based on analysis of samples of the hydrocarbon composition before and after chemical treatment. Actual changes in the hydrocarbon, such as PP temperature, can be quantitatively measured by performing infrared (IR) fingerprint analysis of the samples before and after chemical treatment, which can be used to train chemical additive efficacy predictive models for predicting the efficacy of chemical additives to mitigate the determined wax risks. The one or more chemical additive efficacy predictive models are developed using one or more chemical additive efficacy machine learning algorithms such as principal component analysis (PCA), linear regression, and the like.

FIGS. 6C and 6D illustrate a change in differential scanning calorimetry (DSC) heat traces as an indication of potential efficacies of chemical additives. It can be seen from FIG. 6C that the DSC heat traces of the treated and untreated oil are virtually identical, suggesting minimal interference on the wax precipitation process by the chemical additive and thus minimal to none efficacy. On the contrary, as is shown in FIG. 6D, the heat released during wax precipitation is significantly reduced after chemical treatment, suggesting disturbance of the molecular alignment of waxes by the chemical additive and leading to a significant reduction in the pour point.

Waxing risks may also be reduced by blending two or more separate hydrocarbon samples. An oil producer or refiner which primary employs a hydrocarbon crude with high wax deposition tendencies can blend one or more hydrocarbon crudes with low wax deposition tendencies with the high-wax deposition tendency crude to give a blend with overall reduced wax deposition tendency. The low-wax deposition crude can be blended at a ratio of 1%, 2.5%, 5%, 10%, 15%, 20% or 25% by volume or weight, or at a ratio of from 1-25%, 5-25%, 10-25% or 10-20% by volume or weight.

The methods of determining wax risks described herein can be performed either on or offline during hydrocarbon production, transportation, refining, refined hydrocarbon production, processing, handling, storage, and use. In an offline measurement, wax risks of hydrocarbon samples could be measured on a separated sample from the hydrocarbon stream with devices separated from hydrocarbon plant, and then mitigation steps taken on the hydrocarbon stream. For instance, hydrocarbon streams can be treated with an appropriate chemical additive or blend of additives, or the hydrocarbon streams blended prior to entering the concerned process. In an online process, streams can be measured with or without a sample being withdrawn, for instance, well-bore tubing, pipelines, the pre-heat exchangers and other refinery equipment. In an online process, one or more measurements can be taken in real-time and automatically and/or one or more predictions can be made in real-time and automatically and/or one or more processes can be controlled in real-time and automatically according to the measurement(s) and/or prediction(s). Based on the predicted wax risks, the producer/refiner can add mitigation chemicals to the production tubing, processing tanks, pipelines, desalters, heat exchangers and the like. Mitigation chemical can be added to multiple components as well. In some selected embodiments, the oil producer/refiner can adjust the flow rate, order of blending, temperature, and/or introduction or removal of one or more hydrocarbon streams, of the individual crudes entering the refining stream.

The solutions presented in the present application can be conducted with a time lag, or they can be conducted dynamically, which is essentially in real-time with the use of appropriate computer processors.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for determining wax risks in an oil production, transportation, refining, refined product production, processing and use process and taking steps to mitigate those risks, if necessary. In one exemplary aspect, the units can comprise a computer 700 that comprises a processor 721 as illustrated in FIG. 7 and described below.

Furthermore, all or portions of aspects of the disclosed can be implemented using cloud-based processing and storage systems and capabilities. The computer 700 described in relation to FIG. 7 may comprise a portion of a cloud-based processing and storage system. One such non-limiting example of a cloud-base service that can be used in implementations of the disclosed is GE Predix™, as available from the General Electric Company (Schenectady, N.Y.).

Predix™ is a cloud-based PaaS (platform as a service) that enables industrial-scale analytics for asset performance management (APM) and operations optimization by providing a standard way to connect machines, data, and people.

FIG. 7 illustrates an exemplary computer 700 that can be used for analyzing the sample of the hydrocarbon composition to determine one or more attributes of the sample of the hydrocarbon composition; developing one or more predictive models of a hydrocarbon production, transportation, refining, refined hydrocarbon production, processing, handling, storage, and use of the hydrocarbon composition entering the process of hydrocarbon production, transportation, refining, refined hydrocarbon production, processing, handling, storage, and use based on the analysis of the sample of the hydrocarbon composition; and determining wax risks based on the developed one or more predictive models. In various aspects, the computer of FIG. 7 may comprise all or a portion of the computer 700 and/or a process control system. As used herein, "computer" may include a plurality of computers. The computer 700 may include one or more hardware components such as, for example, a processor 721, a random access memory (RAM) module 722, a read-only memory (ROM) module 723, a storage 724, a database 725, one or more input/output (I/O) devices 726, and an interface 727. Alternatively and/or additionally, the computer 700 may include one or more software components such as, for example, a computer-readable medium including computer executable instructions for performing a method associated with the exemplary embodiments. It is contemplated that one or more of the hardware components listed above may be implemented using software. For example, storage 724 may include a software partition associated with one or more other hardware components. It is understood that the components listed above are exemplary only and not intended to be limiting.

Processor 721 may include one or more processors, each configured to execute instructions and process data to perform one or more functions associated with a processing device for determining wax risks in a hydrocarbon refining process and taking steps to mitigate those risks, if necessary. As used herein, "processor" 721 refers to a physical hardware device that executes encoded instructions for performing functions on inputs and creating outputs. Processor 721 may be communicatively coupled to RAM 722, ROM 723, storage 724, database 725, I/O devices 726, and interface 727. Processor 721 may be configured to execute sequences of computer program instructions to perform various processes. The computer program instructions may be loaded into RAM 722 for execution by processor 721.

RAM 722 and ROM 723 may each include one or more devices for storing information associated with operation of processor 721. For example, ROM 723 may include a memory device configured to access and store information associated with computer 700, including information for identifying, initializing, and monitoring the operation of one or more components and subsystems. RAM 722 may include a memory device for storing data associated with one or more operations of processor 721. For example, ROM 723 may load instructions into RAM 722 for execution by processor 721.

Storage 724 may include any type of mass storage device configured to store information that processor 721 may need to perform processes consistent with the disclosed embodiments. For example, storage 724 may include one or more magnetic and/or optical disk devices, such as hard drives, CD-ROMs, DVD-ROMs, or any other type of mass media device.

Database 725 may include one or more software and/or hardware components that cooperate to store, organize, sort, filter, and/or arrange data used by computer 700 and/or processor 721. It is contemplated that database 725 may store additional and/or different information than that listed above.

I/O devices 726 may include one or more components configured to communicate information with a user associated with computer 700. For example, I/O devices 726 may include a console with an integrated keyboard and mouse to allow a user to maintain an algorithm for analyzing the sample of the hydrocarbon composition to determine one or more attributes of the sample of the hydrocarbon composition; developing one or more predictive models of a hydrocarbon production, transportation, refining, refined hydrocarbon production, processing, handling, storage, and use for the hydrocarbon composition entering the process of hydrocarbon production, transportation, refining, refined hydrocarbon production, processing, handling, storage, and use based on the analysis of the sample of the hydrocarbon composition; and determining wax risks based on the developed one or more predictive models, and the like. I/O devices 726 may also include a display including a graphical user interface (GUI) for outputting information on a monitor. I/O devices 726 may also include peripheral devices such as, for example, a printer for printing information associated with computer 700, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 727 may include one or more components configured to transmit and receive data via a communication network, such as the Internet, a local area network, a workstation peer-to-peer network, a direct link network, a wireless network, or any other suitable communication platform. For example, interface 727 may include one or more modulators, demodulators, multiplexers, demultiplexers, network communication devices, wireless devices, antennas, modems, and any other type of device configured to enable data communication via a communication network.

The disclosed and described embodiments herein are summarized in the lettered paragraphs, below:

A. A method of determining and mitigating wax risk of a hydrocarbon composition comprising: obtaining a sample of the hydrocarbon composition; analyzing the sample of the hydrocarbon composition to determine one or more attributes of the sample of the hydrocarbon composition; developing one or more predictive models of a hydrocarbon production, transportation, refining, refined hydrocarbon production, processing and use process for the hydrocarbon composition entering the hydrocarbon production, transportation, refining, refined hydrocarbon production, processing and use process based on the analysis of the sample of the hydrocarbon composition; determining wax risks based on the developed one or more predictive models; and mitigating one or more of the determined wax risks.

B. The method described in A, further comprising developing a pipe flow model for a pipeline and determining wax risks in the pipeline based on the pipe flow model and the determined wax risks.

C. The method described in B, wherein developing the pipe flow model for the pipeline comprises using parameters and operating conditions of the pipeline when developing the pipe flow model.

D. The method described in C, wherein the parameters and operating conditions of the pipeline comprise real-time parameters and operating conditions of the pipeline.

E. The method of described in any of C and D, wherein the parameters and operating conditions of the pipeline comprise historical parameters and operating conditions of the pipeline.

F. The method described in any of A-E, further comprising determining chemical additives to mitigate one or more of the determined wax risks.

G. The method described in F, wherein determining chemical additives to mitigate one or more of the determined wax risks comprises selecting one or more chemical additives based on matching precipitation characteristics between the one or more chemical additives and wax in the hydrocarbon composition, and/or the attributes related to composition of the hydrocarbon H. The method described in F, further comprising determining a blend of chemical additives to mitigate one or more of the determined wax risks.

I. The method described in H, wherein the blend of chemical additives is determined based on matching precipitation characteristics between the blend of chemical additives and wax in the hydrocarbon composition.

J. The method described in any of G-I, wherein the wax in the hydrocarbon composition is determined based on the analysis of the sample of the hydrocarbon composition to determine the one or more attributes of the sample of the hydrocarbon composition.

K. The method described in F, wherein determining chemical additives to mitigate one or more of the determined wax risks comprises developing qualitative chemical additive predictive models for selecting one or more chemical additives based on the analysis of the sample of the hydrocarbon composition to determine the one or more attributes of the sample of the hydrocarbon composition.

L. The method described in K, wherein the qualitative chemical additive predictive models are developed using a chemical additive machine learning algorithm.

M. The method described in L, wherein the chemical additive machine learning algorithm includes one or more of random decisions forests, principal component analysis (PCA) clustering, k-means clustering, support vector machine (SVM), partial-least squares, neural network, Naïve Bayes classifier, linear discriminant analysis, quadratic discriminant analysis, gradient boosting, boosted trees, or decision trees.

N. The method described in any of F-M, further comprising determining an efficacy of the chemical additives to mitigate one or more of the determined wax risks.

O. The method described in N, wherein determining an efficacy of the chemical additives to mitigate one or more of the determined wax risks comprises determining qualitative and quantitative predictions of pour point depression of the hydrocarbon composition based on analysis of samples of the hydrocarbon composition before and after chemical treatment.

P. The method described in O, wherein the analysis of samples of the hydrocarbon composition before and after chemical treatment comprises performing infrared (IR) fingerprint analysis of the samples before and after chemical treatment.

Q. The method described in P, further comprising developing one or more chemical additive efficacy predictive models based on the IR fingerprint analysis of the samples before and after chemical treatment to predict the efficacy of the chemical additives to mitigate one or more of the determined wax risks.

R. The method described in Q, wherein the one or more chemical additive efficacy predictive models are developed using one or more chemical additive efficacy machine learning algorithms.

S. The method described in R, wherein the one or more chemical additive efficacy machine learning algorithms include principal component analysis (PCA) and linear regression.

T. The method described in any of A-S, wherein analyzing the sample of the hydrocarbon composition to determine one or more attributes of the sample of the hydrocarbon composition comprises performing one or more of fingerprint analysis of the sample, high temperature gas chromatography (HTGC) analysis of the sample, differential scanning calorimetry analysis, inductively coupled plasma mass spectrum analysis or combination of the variable analysis of the sample to determine one or more attributes of the sample.

U. The method described in T, wherein the fingerprint analysis comprises using spectroscopy.

V. The method described in U, wherein the spectroscopy comprises one or more of infrared (IR) spectroscopy, temperature-dependent IR spectroscopy, two-dimensional (2D) spectroscopy, ultra-violet (UV) spectroscopy, near-infrared spectroscopy, mid-infrared spectroscopy, and nuclear magnetic resonance spectroscopy.

W. The method described in any of T-V, wherein the one or more attributes include Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP).

X. The method described in W, wherein one or more of the Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP) are predicted based on one or more measured attributes of the sample of the hydrocarbon composition.

Y. The method described in X, wherein one or more of the attributes are measured using microscopy, UV-vis spectroscopy, light scattering, or acoustic resonance.

Z. The method described in any of T-Y, wherein the fingerprint analysis is performed at a temperature less than a Wax Appearance Temperature (WAT) of the hydrocarbon composition.

AA. The method described in any of A-Z, wherein the one or more predictive models of the hydrocarbon production, transportation, refining, refined hydrocarbon production, processing, handling, storage, and use are developed using one or more machine learning algorithms.

BB. The method described in AA, wherein the one or more machine learning algorithms include principal component analysis (PCA), linear regression and logistic regression.

CC. The method described in any of A-BB, wherein the determined wax risks include one or more of wax content, heavy wax content, Wax Appearance Temperature (WAT), Pour Point (PP), and wax deposition potential.

DD. The method described in any of A-CC, wherein mitigating one or more of the determined wax risks comprises modifying the production, transportation, storage, processing, and/or distribution of the hydrocarbon composition to reduce the determined wax risks.

EE. A method of reducing wax risks in a hydrocarbon composition comprising: obtaining a sample of the hydrocarbon composition; determining one or more wax risks by: analyzing the sample of the hydrocarbon composition to determine one or more attributes of the sample of the hydrocarbon composition; developing one or more predictive models for the hydrocarbon composition based on the analysis of the sample of the hydrocarbon composition; and determining the one or more wax risks based on the developed one or more predictive models; and modifying the production, transportation, storage, processing, and/or distribution of the hydrocarbon composition to reduce the wax risks.

FF. The method described in EE, further comprising developing a pipe flow model for a pipeline and determining wax risks in the pipeline based on the determined wax risks.

GG. The method described in FF, wherein developing the pipe flow model for the pipeline comprises using parameters and operating conditions of the pipeline when developing the pipe flow model.

HH. The method described in GG, wherein the parameters and operating conditions of the pipeline comprise real-time parameters and operating conditions of the pipeline.

II. The method described in any of GG and HH, wherein the parameters and operating conditions of the pipeline comprise historical parameters and operating conditions of the pipeline.

JJ. The method described in any of EE-II, wherein the modification of the production, transportation, storage, processing, and/or distribution of the hydrocarbon composition comprises determining one or more chemical additives to combine with the hydrocarbon composition to mitigate one or more of the determined wax risks.

KK. The method described in JJ, wherein the one or more chemical additives include one or more wetting agents, emulsion breakers, detergents, dispersants, stabilizers, corrosion inhibitors, sulphide or metal-sulphide dissolvers, polymerization inhibitors, antioxidants and metal deactivators or combinations thereof.

LL. The method described in any of JJ and KK, wherein determining chemical additives to mitigate one or more of the determined wax risks comprises selecting one or more chemical additives based on matching precipitation characteristics between the one or more chemical additives and wax in the hydrocarbon composition.

MM. The method described in any of JJ-LL, further comprising determining a blend of chemical additives to mitigate one or more of the determined wax risks.

NN. The method described in MM, wherein the blend of chemical additives is determined based on matching precipitation characteristics between the blend of chemical additives and wax in the hydrocarbon composition.

OO. The method described in any of LL-NN, wherein the wax in the hydrocarbon composition is determined based on the analysis of the sample of the hydrocarbon composition to determine the one or more attributes of the sample of the hydrocarbon composition.

PP. The method described in OO, wherein determining one or more chemical additives to mitigate the determined wax risks comprises developing qualitative chemical additive predictive models for selecting one or more chemical additives based on the analysis of the sample of the hydrocarbon composition to determine the one or more attributes of the sample of the hydrocarbon composition.

QQ. The method described in PP, wherein the qualitative chemical additive predictive models are developed using a chemical additive machine learning algorithm.

RR. The method described in QQ, wherein the chemical additive machine learning algorithm includes one or more of random decisions forests, principal component analysis (PCA) clustering, k-means clustering, support vector machine (SVM), partial-least squares, neural network, Naïve Bayes classifier, linear discriminant analysis, quadratic discriminant analysis, gradient boosting, boosted trees, or decision trees.

SS. The method described in any of JJ-RR, wherein modification of the production, transportation, storage, processing, and/or distribution of the hydrocarbon composition comprises adding the one or more chemical additives to the hydrocarbon composition in an incoming transport system or crude storage tanks, to a hydrocarbon storage tank farm that holds the crude oil entering the process of hydrocarbon production, transportation, refining, refined hydrocarbon production, processing, handling, storage, and use, to a water wash, to a de-salter, to a hot preheat train after desalting of the refining process, or combinations thereof.

TT. The method described in any of JJ-SS, further comprising determining an efficacy of the chemical additives to mitigate one or more of the determined wax risks.

UU. The method described in TT, wherein determining an efficacy of the chemical additives to mitigate one or more of the determined wax risks comprises determining qualitative and quantitative predictions of pour point depression of the hydrocarbon composition based on analysis of samples of the hydrocarbon composition before and after chemical treatment.

VV. The method described in UU, wherein the analysis of samples of the hydrocarbon composition before and after chemical treatment comprises performing infrared (IR) fingerprint analysis of the samples before and after chemical treatment.

WW. The method described in VV, further comprising developing one or more chemical additive efficacy predictive models based on the IR fingerprint analysis of the samples before and after chemical treatment to predict the efficacy of the chemical additives to mitigate one or more of the determined wax risks.

XX. The method described in WW, wherein the one or more chemical additive efficacy predictive models are developed using one or more chemical additive efficacy machine learning algorithms.

YY. The method described in XX, wherein the one or more chemical additive efficacy machine learning algorithms include principal component analysis (PCA) and linear regression.

ZZ. The method described in any of EE-YY, wherein analyzing the sample of the hydrocarbon composition to determine one or more attributes of the sample of the hydrocarbon composition comprises performing one or more of fingerprint analysis of the sample, high temperature gas chromatography (HTGC) analysis of the sample, differential scanning calorimetry analysis, inductively coupled plasma mass spectrum analysis or combination of the variable analysis of the sample to determine one or more attributes of the sample.

AAA. The method described in ZZ, wherein the fingerprint analysis comprises using spectroscopy.

BBB. The method described in AAA, wherein the spectroscopy comprises one or more of infrared (IR) spectroscopy, temperature-dependent IR spectroscopy, two-dimensional (2D) spectroscopy, ultra-violet (UV) spectroscopy, near-infrared spectroscopy, mid-infrared spectroscopy, and nuclear magnetic resonance spectroscopy.

CCC. The method described in any of ZZ-BBB, wherein the one or more attributes include Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP).

DDD. The method described in CCC, wherein one or more of the Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP) are predicted based on one or more measured attributes of the sample of the hydrocarbon composition.

EEE. The method described in DDD, wherein one or more of the attributes are measured using microscopy, UV-vis spectroscopy, light scattering, or acoustic resonance.

FFF. The method described in any of ZZ-EEE, wherein the fingerprint analysis is performed at a temperature less than a Wax Appearance Temperature (WAT) for the hydrocarbon composition.

GGG. The method described in any one of EE-FFF, wherein the one or more predictive models of the hydrocarbon refining are developed using one or more machine learning algorithms.

HHH. The method described in GGG, wherein the one or more machine learning algorithms include principal component analysis (PCA), linear regression and logistic regression.

III. The method described in any of EE-HHH, wherein the determined wax risks include one or more of Wax Appearance Temperature (WAT), Pour Point (PP), and wax deposition potential.

JJJ. The method described in any of EE-III, wherein developing one or more predictive models for the hydrocarbon composition comprises developing on or more predictive models for production, transportation, refining, refined hydrocarbon production, processing, handling, storage, use for the hydrocarbon composition; one or more predictive models for the hydrocarbon composition entering a process of hydrocarbon production, transportation, refining, refined hydrocarbon production, processing, handling, storage, and use; or one or more predictive models for the hydrocarbon composition as the hydrocarbon composition moves through the process of hydrocarbon production, transportation, refining, refined hydrocarbon production, processing, handling, storage, and use; each predictive model based on the analysis of the sample of the hydrocarbon composition.

KKK. A system for using predictive analytics in management of a hydrocarbon process, said system comprising: a memory, wherein the memory stores computer-readable instructions; and a processor communicatively coupled with the memory, wherein the processor executes the computer-readable instructions stored on the memory, the computer-readable instructions causing the processor to: receive an analysis of a hydrocarbon sample, develop one or more predictive models for a hydrocarbon based on one or more attributes of the sample of the hydrocarbon composition determined in the analysis of the hydrocarbon sample; determine wax risks based on the developed one or more predictive models; and control aspects of the hydrocarbon process based on the determined wax risks to mitigate one or more of the determined wax risks, wherein the analysis is obtained by the following steps: obtaining a sample of the hydrocarbon composition; and analyzing the sample of the hydrocarbon composition to determine the one or more attributes of the sample of the hydrocarbon composition.

LLL. The system described in KKK, further comprising causing the processor to execute instructions to develop a pipe flow model for a pipeline and determine wax risks in the pipeline based on the determined wax risks.

MMM. The system described in LLL, wherein developing the pipe flow model for the pipeline comprises causing the processor to execute instructions to receive and use parameters and operating conditions of the pipeline when developing the pipe flow model.

NNN. The system described in MMM, wherein the parameters and operating conditions of the pipeline are received by the processor in real-time.

OOO. The system described in any of MMM and NNN, wherein the parameters and operating conditions of the pipeline comprise historical parameters and operating conditions of the pipeline that are retrieved from the memory and supplied to the processor.

PPP. The system described in any of KKK-OOO, wherein managing aspects of the hydrocarbon process comprises causing the processor to execute instructions to determine one or more chemical additives to combine with the hydrocarbon composition to mitigate the determined wax risks.

QQQ. The system described in PPP, wherein the one or more chemical additives include one or more wetting agents, emulsion breakers, detergents, dispersants, stabilizers, corrosion inhibitors, sulphide or metal-sulphide dissolvers, polymerization inhibitors, antioxidants and metal deactivators or combinations thereof.

RRR. The system described in any of PPP and QQQ, wherein the processor determining chemical additives to mitigate the determined wax risks comprises causing the processor to execute instructions to select one or more chemical additives based on matching precipitation characteristics between the one or more chemical additives and wax in the hydrocarbon composition.

SSS. The system described in any of PPP-RRR, further comprising causing the processor to execute instructions to determine a blend of chemical additives to mitigate the determined wax risks.

TTT. The system described in SSS, wherein the blend of chemical additives is determined based on causing the processor to execute instructions to match precipitation characteristics between the blend of chemical additives and wax in the hydrocarbon composition.

UUU. The system described in any of RRR-TTT, wherein the wax in the hydrocarbon composition is determined by the processor based on the received analysis of the sample of the hydrocarbon composition.

VVV. The system described in UUU, wherein causing the processor to execute instructions to determine one or more chemical additives to mitigate the determined wax risks comprises causing the processor to execute instructions to develop qualitative chemical additive predictive models for selecting one or more chemical additives based on the received analysis of the sample of the hydrocarbon composition.

WWW. The system described in VVV, wherein the qualitative chemical additive predictive models are developed by the processor executing instructions that comprise one or more chemical additive machine learning algorithms.

XXX. The system described in WWW, wherein the chemical additive machine learning algorithm includes one or more of random decisions forests, principal component analysis (PCA) clustering, k-means clustering, support vector machine (SVM), partial-least squares, neural network, Naïve Bayes classifier, linear discriminant analysis, quadratic discriminant analysis, gradient boosting, boosted trees, or decision trees.

YYY. The system described in any of PPP-XXX, wherein controlling aspects of the hydrocarbon process comprises causing the processor to execute instructions to add the one or more chemical additives to the hydrocarbon composition.

ZZZ. The system described in any of PPP-YYY, further comprising causing the processor to execute instructions to determine an efficacy of the chemical additives to mitigate the determined wax risks.

AAAA. The system described in ZZZ, wherein determining an efficacy of the chemical additives to mitigate the determined wax risks comprises causing the processor to execute instructions to determine qualitative and quantitative predictions of pour point depression of the hydrocarbon composition based on analysis of samples of the hydrocarbon composition before and after chemical treatment.

BBBB. The system described in AAAA, wherein the analysis of samples of the hydrocarbon composition before and after chemical treatment comprises causing the processor to execute instructions to perform infrared (IR) fingerprint analysis of the samples before and after chemical treatment.

CCCC. The system described in BBBB, further comprising causing the processor to execute instructions to develop one or more chemical additive efficacy predictive models based on the IR fingerprint analysis of the samples before and after chemical treatment to predict the efficacy of the chemical additives to mitigate the determined wax risks.

DDDD. The system described in CCCC, wherein the one or more chemical additive efficacy predictive models are developed by the processer executing instructions that comprise one or more chemical additive efficacy machine learning algorithms.

EEEE. The system described in DDDD, wherein the one or more chemical additive efficacy machine learning algorithms include causing the processor to execute instructions to perform principal component analysis (PCA) or linear regression analysis.

FFFF. The system described in any of KKK-EEEE, wherein analyzing the sample of the hydrocarbon composition to determine one or more attributes of the sample of the hydrocarbon composition comprises performing one or more of fingerprint analysis of the sample, high temperature gas chromatography (HTGC) analysis of the sample, differential scanning calorimetry analysis, inductively coupled plasma mass spectrum analysis or combination of the variable analysis of the sample to determine one or more attributes of the sample.

GGGG. The system described in FFFF, wherein the fingerprint analysis comprises using spectroscopy.

HHHH. The system described in GGGG, wherein the spectroscopy comprises one or more of infrared (IR) spectroscopy, temperature-dependent IR spectroscopy, two-dimensional (2D) spectroscopy, ultra-violet (UV) spectroscopy, near-infrared spectroscopy, mid-infrared spectroscopy, and nuclear magnetic resonance spectroscopy.

IIII. The system described in any of FFFF-HHHH, wherein the one or more attributes include Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP).

JJJJ. The system described in IIII, wherein one or more of the Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP) are predicted based on one or more measured attributes of the sample of the hydrocarbon composition.

KKKK. The system described in JJJJ, wherein one or more of the attributes are measured using microscopy, UV-vis spectroscopy, light scattering, or acoustic resonance.

LLLL. The system described in any of FFFF-LLLL, wherein the fingerprint analysis is performed at a temperature less than a Wax Appearance Temperature (WAT) of the hydrocarbon composition.

MMMM. The system described in any one of KKK-LLLL, wherein the one or more predictive models of the hydrocarbon refining are developed by the processor executing instructions that comprise one or more machine learning algorithms.

NNNN. The system described in MMMM, wherein the one or more machine learning algorithms include principal component analysis (PCA), linear regression and logistic regression.

OOOO. The system described in any of KKK-NNNN, wherein the causing the processor to execute instructions to determine wax risks comprises determining one or more of Wax Appearance Temperature (WAT), Pour Point (PP), and wax deposition potential.

PPPP. The system described in any one of KKK-OOOO, wherein controlling aspects of the hydrocarbon process based on the determined wax risks to mitigate one or more of the determined wax risks comprises controlling one or more of hydrocarbon production, transportation, refining, refined hydrocarbon production, processing, handling, storage, and use as the hydrocarbon composition enters the production, transportation, refining, refined hydrocarbon production, processing, handling, storage, and use or moves through the production, transportation, refining, refined hydrocarbon production, processing, handling, storage, and use.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of determining and mitigating wax risk of a hydrocarbon composition, the method comprising:
    obtaining a sample of the hydrocarbon composition;
    analyzing the sample of the hydrocarbon composition to determine one or more attributes of the sample of the hydrocarbon composition;
    developing a first predictive model representative of hydrocarbon production, transportation, refining, refined hydrocarbon production, and/or processing based on the analysis of the sample of the hydrocarbon composition, wherein the first predictive model is developed using one or more machine learning algorithms;
    determining wax risks based on the first predictive model;
    developing, using the one or more machine learning algorithms, a second predictive model for selecting one or more chemical additives to add to the hydrocarbon composition based on the determined wax risks; and
    mitigating one or more of the determined wax risks by introducing the one or more chemical additives during at least one of the production, transportation, storage, processing, or distribution of the hydrocarbon composition.

2. The method of claim 1, wherein the second predictive model is a pipe flow model for a pipeline and wherein the one or more chemical additives are selected based on the pipe flow model and the determined wax risks.

3. The method of claim 1, wherein the one or more chemical additives are selected based on matching precipitation characteristics between the one or more chemical additives and wax in the hydrocarbon composition, and/or the attributes related to composition of the hydrocarbon.

4. The method of claim 1, wherein analyzing the sample of the hydrocarbon composition to determine one or more attributes of the sample of the hydrocarbon composition comprises performing one or more of fingerprint analysis of the sample, high temperature gas chromatography (HTGC) analysis of the sample, differential scanning calorimetry analysis, or inductively coupled plasma mass spectrum analysis of the sample to determine one or more attributes of the sample.

5. The method of claim 1, wherein the one or more attributes include Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP).

6. The method of claim 1, wherein the one or more machine learning algorithms include principal component analysis (PCA), linear regression and logistic regression.

7. The method of claim 1, wherein the determined wax risks include one or more of wax content, heavy wax content, Wax Appearance Temperature (WAT), Pour Point (PP), and wax deposition potential.

8. The method of claim 1, wherein mitigating one or more of the determined wax risks further comprises modifying the production, transportation, storage, processing, and/or distribution of the hydrocarbon composition to reduce the determined wax risks.

9. A method of reducing wax risks in a hydrocarbon composition, the method comprising:
obtaining a sample of the hydrocarbon composition;
determining one or more wax risks by:
analyzing the sample of the hydrocarbon composition to determine one or more attributes of the sample of the hydrocarbon composition;
developing a first predictive model for the hydrocarbon composition based on the analysis of the sample of the hydrocarbon composition, wherein the first predictive model is developed using one or more machine learning algorithms;
determining the wax risks using the first predictive model;
developing, using the one or more machine learning algorithms, a second predictive model for selecting one or more chemical additives to add to the hydrocarbon composition based on the determined wax risks; and
introducing the one or more chemical additives during at least one of production, transportation, storage, processing, and/or distribution of the hydrocarbon composition to reduce the wax risks.

10. The method of claim 9, wherein the second predictive model is a pipe flow model for a pipeline and wherein the one or more chemical additives are selected based on the pipe flow model and the determined wax risks.

11. The method of claim 9, wherein the one or more chemical additives are selected based on matching precipitation characteristics between the one or more chemical additives and wax in the hydrocarbon composition, and/or the attributes related to composition of the hydrocarbon.

12. The method of claim 9, wherein analyzing the sample of the hydrocarbon composition to determine one or more attributes of the sample of the hydrocarbon composition comprises performing one or more of fingerprint analysis of the sample, high temperature gas chromatography (HTGC) analysis of the sample, differential scanning calorimetry analysis, or inductively coupled plasma mass spectrum analysis of the sample to determine one or more attributes of the sample.

13. The method of claim 9, wherein the one or more machine learning algorithms include principal component analysis (PCA), linear regression and logistic regression.

14. The method of claim 9, wherein the determined wax risks include one or more of Wax Appearance Temperature (WAT), Pour Point (PP), wax content, heavy wax content, and wax deposition potential.

15. A system for using predictive analytics in management of a hydrocarbon process, said system comprising:
a memory, wherein the memory stores computer-readable instructions; and
a processor communicatively coupled with the memory, wherein the processor executes the computer-readable instructions stored on the memory, the computer-readable instructions causing the processor to:
receive an analysis of a hydrocarbon sample,
develop a first predictive model for a hydrocarbon based on one or more attributes of the sample of the hydrocarbon composition determined in the analysis of the hydrocarbon sample, wherein the first predictive model is developed using one or more machine learning algorithms;
determine the wax risks using the predictive model;
develop, using the one or more machine learning algorithms, a second predictive model for selecting one or more chemical additives to add to the hydrocarbon composition based on the determined wax risks; and
control aspects of the hydrocarbon process based on the determined wax risks to mitigate one or more of the determined wax risks by, at least, introducing the one or more chemical additives during at least one of production, transportation, storage, processing, or distribution of the hydrocarbon composition;
wherein the analysis is obtained by the following steps:
obtaining a sample of the hydrocarbon composition; and
analyzing the sample of the hydrocarbon composition to determine the one or more attributes of the sample of the hydrocarbon composition.

16. The system of claim 15, wherein the second predictive model is a pipe flow model for a pipeline and wherein the one or more chemical additives are selected based on the determined wax risks.

17. The system of claim 15, wherein the one or more chemical additives are selected based on matching precipitation characteristics between the one or more chemical additives and wax in the hydrocarbon composition.

18. The system of claim 15, wherein analyzing the sample of the hydrocarbon composition to determine one or more attributes of the sample of the hydrocarbon composition comprises performing one or more of fingerprint analysis of the sample, high temperature gas chromatography (HTGC) analysis of the sample, differential scanning calorimetry analysis, or inductively coupled plasma mass spectrum analysis of the sample to determine one or more attributes of the sample.

19. The system of claim 15, wherein the one or more attributes include Total Acid Number (TAN), American Petroleum Institute gravity (API gravity), specific gravity (SG), SARA (saturates, aromatics, resins, asphaltenes), Colloid Instability Index (CII), viscosity, rheology, wax content, heavy wax content, Wax Appearance Temperature (WAT), and Pour Point (PP).

20. The system of claim 15, wherein the one or more machine learning algorithms include principal component analysis (PCA), linear regression and logistic regression.

21. The system of claim 15, wherein the causing the processor to execute instructions to determine wax risks comprises determining one or more of Wax Appearance Temperature (WAT), Pour Point (PP), wax content, heavy wax content and wax deposition potential.

* * * * *